US006632823B1

(12) United States Patent
Vernier et al.

(10) Patent No.: US 6,632,823 B1
(45) Date of Patent: Oct. 14, 2003

(54) SUBSTITUTED PYRIDINE COMPOUNDS USEFUL AS MODULATORS OF ACETYLCHOLINE RECEPTORS

(75) Inventors: Jean-Michel Vernier, San Diego, CA (US); Nicholas D. P. Cosford, San Diego, CA (US); Ian A. McDonald, San Diego, CA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 08/996,308

(22) Filed: Dec. 22, 1997

(51) Int. Cl.[7] ............... C07D 213/00; C07D 221/02; C07D 401/00; C07D 453/02
(52) U.S. Cl. ............... 514/304; 546/288; 546/289; 546/290; 546/293; 546/296; 546/297; 546/298; 546/300; 546/301; 546/302; 546/303; 546/306; 546/307; 546/308; 546/309; 546/310; 546/312; 546/314; 546/323; 546/326; 546/328; 546/329; 546/333; 546/334; 546/335; 546/336; 546/337
(58) Field of Search ............... 514/299, 304, 514/305, 306, 318, 339, 340, 343, 344, 346, 348, 349, 351, 352, 353, 357, 350; 546/125, 133, 137, 138, 183, 193, 268.1, 276.4, 276.7, 278.4, 286, 287, 288, 289, 290, 293, 296, 297, 298, 300, 301, 302, 303, 304, 306, 307, 308, 309, 310, 312, 314, 323, 326, 328, 329, 333, 334, 335, 336, 337, 338

(56) References Cited

U.S. PATENT DOCUMENTS

| | | | |
|---|---|---|---|
| 3,370,059 A | | 2/1968 | Schuler et al. ............ 260/247.1 |
| 3,821,216 A | * | 6/1974 | Domenico ............... 260/247.1 |
| 4,643,995 A | | 2/1987 | Engel et al. ................ 514/210 |
| 5,214,060 A | | 5/1993 | Caldwell et al. ........... 514/343 |
| 5,232,933 A | | 8/1993 | Lippiello et al. ........... 514/343 |
| 5,369,028 A | | 11/1994 | Harpold et al. .......... 435/252.3 |
| 5,691,364 A | * | 11/1997 | Buckman et al. .......... 514/341 |
| 5,948,793 A | * | 9/1999 | Abreo et al. ............... 514/318 |
| 5,998,429 A | * | 12/1999 | Macor et al. .............. 514/299 |
| 6,054,464 A | * | 4/2000 | Macor et al. .............. 514/299 |

FOREIGN PATENT DOCUMENTS

| | | | | |
|---|---|---|---|---|
| DE | 25 03 136 A1 | | 7/1975 | |
| DE | 44 25 143 A1 | | 1/1996 | |
| DE | 44 25 146 A 1 | | 1/1996 | ......... A61K/31/495 |
| EP | 0 149 088 | * | 7/1985 | |
| EP | 0 191 603 | * | 8/1986 | |
| EP | 0 559 414 A1 | | 9/1993 | ......... A61K/31/465 |
| EP | 0 682 016 A1 | | 11/1995 | ......... C07D/213/76 |
| JP | 9-241161 | | 3/1996 | ......... A61K/31/505 |
| WO | WO 89/00566 | * | 1/1989 | |
| WO | WO 91/15602 | | 10/1991 | ............ C12Q/1/68 |
| WO | WO 92/04333 A1 | | 3/1992 | |
| WO | WO 94/20617 | | 9/1994 | ........... C12N/15/12 |
| WO | WO 96/41876 | | 12/1996 | ........... C12N/15/12 |
| WO | WO 97/11072 | | 3/1997 | ......... C07D/453/02 |

OTHER PUBLICATIONS

Hood et al., Enhancement of Analgesia from Systemic Opioid in Humans by Spinal Cholinesterase Inhibition, The Journal of Pharmaceutical and Experimental Therapeutics, Jul. 1997, vol. 282, No. 1, pp. 86–92.*
Sullivan et al., (+–)–Epibatidine Elicits a Diversity of In Vitro and In Vivo Effects Mediated by Nicotinic Acetylcholine Receptors, The Journal of Pharmacology and Experimental Therapeutics, vol. 271, No. 2, pp. 624–631, Nov. 1994.*
HCAPLUS printout for WO 89/00566, Jan. 1989.*
Banks et al., Heterocyclic Polyfluoro–compounds, J. Chem. Soc. (C), vol. 12, pp. 1660–1662, 1969.*
Roberts et al., Polychloroaromatic Compounds, J. Chem. Soc. (C), vol. 12, pp. 1537–1541, 1968.*
Roberts et al., Peroxy–acid Oxidation of NN–Disubstituted Aminotetrafluoro–, Amino–3–chlorotrifluoror– and Amino–3,5–dichlorodifluoro–pyridines, J. Chem. Soc. (C), vol. 12, pp. 1485–1491, 1969.*
Aaron and Reiff, "Synthesis of 6α–Tropanol" *J. Heterocycl. Chem.* (5) 423–424 (1968).
Albanese, et al., "Chronic Administration of 1–Methyl–4–Phenyl–1,2,3,6–Tetrahydrophyridine to Monkeys: Behavioural, Morphological and Biochemical Correlates" *Neuroscience* 55(3):823–832 (1993).

(List continued on next page.)

*Primary Examiner*—Brenda Coleman
(74) *Attorney, Agent, or Firm*—David Rubin; David L. Rose

(57) ABSTRACT

In accordance with the present invention, a novel class of substituted pyridine compounds (optionally containing ether, ester, amide, ketone or thioether substitutions) that promote the release of ligands involved in neurotransmission have been discovered. In a particular aspect compounds of the present invention are capable of modulating acetylcholine receptors. The compounds of the present invention are capable of modulating acetylcholine receptors. Invention compounds may act as agonists, partial agonists, antagonists or allosteric modulators of acetylcholine receptors. Therapeutic indications for compounds with activity at acetylcholine receptors include diseases of the central nervous system such as Alzheimer's disease and other diseases involving memory loss and/or dementia (including AIDS dementia); cognitive dysfunction (including disorders of attention, focus and concentration), disorders of extrapyramidal motor function such as Parkinson's disease, progressive supramuscular palsy, Huntington's disease, Gilles de la Tourette syndrome and tardive dyskinesia; mood and emotional disorders such as depression, anxiety and psychosis; substance abuse including withdrawal symptoms and substitution therapy; neurocrine disorders and dysregulation of food intake, including bulimia and anorexia; disorders or nociception and control of pain; autonomic disorders including dysfunction of gastrointestinal motility and function such as inflammatory bowel disease, irritable bowel syndrome, diarrhea, constipation, gastric acid secretion and ulcers; pheochromocytoma, cardiovascular dysfunction including hypertension and cardiac arrhythmias, as well as co-medication uses in surgical applications.

19 Claims, No Drawings

OTHER PUBLICATIONS

Brioni, et al., "Nicotinic receptor agonists exhibit anxiolytic–like effects on the elevated plus–maze test" *Euroepan Journal Pharmacology* 238:1–8 (1993).

Christensen, et al., "On the Supersensitivity of Dopamine Receptors, Induced by Neuroleptics" *Psycho–pharmacology* 48:1–6 (1976).

Clow, et al., "Changes in Dopamine–Mediated Behaviour During One Year's Neuroleptic Administration" *European Journal of Pharmacology* 57:365–375 (1979).

Colpaert, F. C., "Pharmacological Characteristics of Tremor, Rigidity and Hypokinesia Induced by Reserpine in Rat" *Neuropharmacology* 26 (9):1431–1440 (1987).

Coyle, et al., "Kainic Acid: Insights From a Neurotoxin into the Pathophysiology of Huntington's Disease" *Neurobehavioral Toxicology and Teratology* 5:617–624 (1983).

Emerich, et al., "Nicotine Potentiates Haloperidol–Induced Catalepsy and Locomotor Hypoactivity" *Pharmacology Biochemistry & Behavior,* 38:875–880 (1991).

Estrella, et al., "A further study of the neuromuscular effects of vesamicol (AH5183) and of its enantiomer specificity" *Br. J. Pharmacol* 93:759–768 (1988).

Fletcher, et al., "Total Synthesis and Determination of the Absolute Configuration of Epibatidine" *J. Org. Chem.* 59:1771–1778 (1994).

Flynn and Mash, "Characterization of L–[$^3$H]Nicotine Binding in Human Cerebral Cortex: Comparison Between Alzheimer's Disease and the Normal" *Journal Neurochemistry* 47:1948–1954 (1986).

Fürst and Koller, "Ein neuer Weg zur Herstellung der α–Oxyde von Cholesterin und trans–Dehydro–androsteron" *Helvetica Chimica Acta.* 30:1454–1457 (1947).

Gaul and Fremuth, "Sulfur Heterocycles. II. 3–Aryl– and 3–Alkyl–2–thiazolidinone 1,1–Dioxides: New Class of Cyclic Sulfone" *J. Org. Chem.* 26:5103–5105 (1961).

Gautier, et al., "Isolement des bases organiques à l'état de thiocyanates" *Annales pharmaceutiques francaises* 30 (10):715–718 (1972).

Iwamoto, E. T., "Antinociception after Nicotine Administration into the Mesopontine Tegmentum of Rats: Evidence for Muscarinic Actions[1]*The Journal of Pharmacology and Experimental Therapeutics*" 251:412–421 (1989).

Janson, et al., "Differential effects of acute and chronic nicotine treatment on MPTP–(1–methyl–4–phenyl–1,2,3, 6–tetrahydropyridine) induced degeneration of nigrostriatal dopamine neurons in the black mouse" *Clinical Investigatpr* 70:232–238 (1992).

Klockgether and Turski, "NMDA Antagonists Potentiate Antiparkinsonian Actions of L–Dopa in Monoamine–depleted Rats" *Annals of Neurology* 28 (4):539–546 (1990).

Levin, et al., "An Alternative Procedure for the Aluminum–Mediated Conversion of Esters to Amides" *Synthetic Communications* 12 (13):989–993 (1982).

Madesclaire, M., "Synthesis of Sulfoxides by Oxidation of Thioethers" *Tetrahedron* 42 (20):5459–5459 (1986).

Miyata, et al., "Role of the Serotinin$_3$ Receptor in Stress–Induced Defecation" *The Journal of Pharmacology and Experimental Therapeutics* 261 (1):297–303 (1992).

Nahm and Weinreb, "N–Methoxy–N–Methylamides as Effective Acylating Agents" *Tetrahedron Letters* 22 (39):3815–3818 (1981).

Pellow, et al., "Validation of open : closed arm entries in an elevated plus–maze as a measure of anxiety in the rat" *Journal of Neuroscience Methods* 14:149–167 (1985).

Rupniak, et al., "Cholinergic Manipulation of Perioral Behaviour Induced by Chronic Neuroleptic Administration to Rats" *Psychopharmacology* 79:226–230 (1983).

Scaan, et al., "Pharmacological Characterization of Neuronal Acetylcholine Gated Ion Channel Receptor–Mediated Hippocampal Norepinephrine and Striatal Dopamine Release from Rat Brain Slices" *The Journal of Pharmacology and Experimental Therapeutics* 274(1):224–230 (1995).

Schwarz, et al., "Quinolinic Acid: An Endogenous Metabolite That Produces Axon–Sparining Lesions in Rat Brain" *Science* 219:316–318 (1983).

Sershen, et al., "Behavioral and Biochemical Effects of Nicotine in an MPTP–Induced Mouse Model of Parkinson's Disease" *Pharmacology Biochemistry & Behavior* 28:299–303 (1987).

Sundström, et al., "Chronic neurochemical and behavioral changes in MPTP–lesioned C57BL/6 mice: a model for Parkinson's disease" *Brain Research* 528:181–188 (1990).

Tabushi, et al., "The First Anion Capped β–Cyclodextrin for the Effective Inclusion Binding of Hydrophobic Cationic Molecules" *Tetrahedron Letters* 31(48):7017–7020 (1990).

Ungerstedt and Arbuthknott, "Quantitative Recording or Rotational Behavior in Rats After 6–Hydroxy–Dopamine Lesions of the Nigrostriatal Dopamine System" *Brain Research* 24:485–493 (1970).

Von Voigtlander and Moore, "Turning Behavior of Mice with Unilateral 6–Hydroxydopamine Lesions in the Striatum: Effects of Apomorphine, L–Dopa, Amantadine, Ampethamine and Other Psychomotor Stimulants" *Neuropharmacology* 12:451–462 (1973).

Waddington, et al., "Spontaneous Orofacial Dyskinesia and Dopaminergic Function in Rats After 6 Months of Neuroleptic Treatment" *Science* 220:530–532 (1983).

Williams, et al., "Stress–Induced Changes in Intestinal Transit in the Rat: A Model for Irritable Bowel Syndrome" *Gastroenterology* 94:611–621 (1988).

Wróbel ahd Hejchman, "Spiro Derivatives of Tetrahydrothiophene. Synthesis of the Quinolizidine <3–spiro–2'>tetrahydrothiophene System Using Solid/Liquid or Liquid/Liquid Phase–Transfer Catalysis" *Synthesis* 5:452–455 (1987).

Yamada and Onoda, "Effects of a thienylalkylamine derivative, T–1815, on colonic propulsion in mice and rats" *Pharmacological Research Laboratory* (1993).

\* cited by examiner

SUBSTITUTED PYRIDINE COMPOUNDS USEFUL AS MODULATORS OF ACETYLCHOLINE RECEPTORS

The present invention relates to compounds which potentiate neurotransmission by promoting the release of neurotransmitters such as acetylcholine, dopamine and norepinephrine. More particularly, the present invention relates to compounds that are capable of modulating acetylcholine receptors. Invention compounds are useful, for example, for treatment of dysfunction of the central and autonomic nervous systems (e.g. dementia, cognitive disorders, neurodegenerative disorders, extrapyramidal disorders, convulsive disorders, cardiovascular disorders, endocrine disorders, pain, eating disorders, affective disorders, drug abuse, and the like). Invention compounds are also expected to exhibit neuroprotective effects. In addition, the present invention relates to pharmaceutical compositions containing these compounds, as well as various uses therefor.

BACKGROUND OF THE INVENTION

By modulating neurotransmitter release (including dopamine, norepinephrine, acetylcholine and serotonin) from different brain regions, acetylcholine receptors are involved in the modulation of neuroendocrine function, respiration, mood, motor control and function, focus and attention, concentration, memory and cognition, and the mechanisms of substance abuse. Ligands for acetylcholine receptors have been demonstrated to have effects on attention, cognition, appetite, substance abuse, memory, extrapyramidal function, cardiovascular function, pain, gastrointestinal motility and function, as well as exhibiting neuroprotective effects. The distribution of acetylcholine receptors that bind nicotine, i.e., nicotinic acetylcholine receptors, is widespread in the brain, including the basal ganglia, limbic system, cerebral cortex and mid- and hindbrain nuclei. In the periphery, the distribution includes muscle, autonomic ganglia, the gastrointestinal tract and the cardiovascular system.

Acetylcholine receptors have been shown to be decreased, inter alia, in the brains of patients suffering from Alzheimer's disease or Parkinson's disease, diseases associated with dementia, motor dysfunction and cognitive impairment. Such correlations between acetylcholine receptors and nervous system disorders suggest that compounds that modulate acetylcholine receptors will have beneficial therapeutic effects for many human nervous system disorders. Thus, there is a continuing need for compounds which have the ability to modulate the activity of acetylcholine receptors. In response to such need, the present invention provides a new family of compounds which modulate acetylcholine receptors.

BRIEF DESCRIPTION OF THE INVENTION

In accordance with the present invention, we have discovered a novel class of substituted pyridine compounds (containing an ether, ester, amide, ketone or thioether functionality) that promote the release of ligands involved in neurotransmission. More particularly, compounds of the present invention are capable of modulating acetylcholine receptors.

The compounds of the present invention are capable of displacing one or more acetylcholine receptor ligands, e.g., $^3$H-nicotine, from mammalian neuronal membrane binding sites. In addition, invention compounds display activity in cell lines which express recombinant acetylcholine receptors. It can readily be seen, therefore, that invention compounds may act as agonists, partial agonists, antagonists or allosteric modulators of acetylcholine receptors. Therapeutic indications for compounds with activity at acetylcholine receptors include diseases of the central nervous system such as Alzheimer's disease and other diseases involving memory loss and/or dementia (including AIDS dementia); cognitive dysfunction (including disorders of attention, focus and concentration), disorders of extrapyramidal motor function such as Parkinson's disease, progressive supramuscular palsy, Huntington's disease, Gilles de la Tourette syndrome and tardive dyskinesia; mood and emotional disorders such as depression, anxiety and psychosis; substance abuse including withdrawal symptoms and substitution therapy; neurocrine disorders and dysregulation of food intake, including bulimia and anorexia; disorders or nociception and control of pain; autonomic disorders including dysfunction of gastrointestinal motility and function such as inflammatory bowel disease, irritable bowel syndrome, diarrhea, constipation, gastric acid secretion and ulcers; phaeochromocytoma, cardiovascular dysfunction including hypertension and cardiac arrhythmias, as well as co-medication uses in surgical applications. Compounds with activity at acetylcholine receptors have also been shown to have neuroprotective effects.

DETAILED DESCRIPTION OF THE INVENTION

In accordance with the present invention, there are provided methods of modulating the activity of acetylcholine receptors. As employed herein, the phrase "modulating the activity of acetylcholine receptors" refers to a variety of therapeutic applications, such as the treatment of Alzheimer's disease and other disorders involving memory loss and/or dementia (including AIDS dementia); cognitive dysfunction (including disorders of attention, focus and concentration), disorders of extrapyramidal motor function such as Parkinson's disease, progressive supramuscular palsy, Huntington's disease, Gilles de la Tourette syndrome and tardive dyskinesia; mood and emotional disorders such as depression, panic, anxiety and psychosis; substance abuse including withdrawal syndromes and substitution therapy; neuroendocrine disorders and dysregulation of food intake, including bulimia and anorexia; disorders of nociception and control of pain; neuroprotection; autonomic disorders including dysfunction of gastrointestinal motility and function such as inflammatory bowel disease, irritable bowel syndrome, diarrhea, constipation, gastric acid secretion and ulcers; pheochromocytoma; cardiovascular dysfunction including hypertension and cardiac arrhythmias, comedication in surgical procedures, and the like.

The compounds of the present invention are especially useful for the treatment of Alzheimer's disease as well as other types of dementia (including dementia associated with AIDS), Parkinson's disease, cognitive dysfunction (including disorders of attention, focus and concentration), attention deficit syndrome, affective disorders, and for the control of pain. Thus modulation of the activity of acetylcholine receptors present on or within the cells of a patient suffering from any of the above-described indications will impart a therapeutic effect.

Invention methods comprise contacting cell-associated acetylcholine receptors with a concentration of a compound of Formula Z sufficient to modulate the activity of said acetylcholine receptors, compounds having Formula Z being defined as follows:

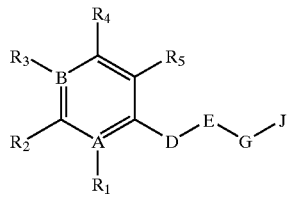

(Z)

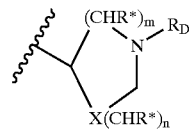

J"

or enantiomers, diastereomeric isomers or mixtures of any two or more thereof, or pharmaceutically acceptable salts thereof, wherein:

A and B are independently selected from —N— or —C—, with the proviso that one of A and B is —N—;

each of $R_1$, $R_2$, $R_3$, $R_4$ and $R_5$ are independently selected from hydrogen, halogen, cyano, cyanomethyl, nitro, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, heterocyclic, substituted heterocyclic, trifluoromethyl, pentafluoroethyl, —$OR_A$, —O—C(O)—$R_A$, —O—C(O)—N($R_A$)$_2$, —$SR_A$, —NHC(O)$R_A$ or —NHSO$_2R_A$, wherein $R_A$ is selected from H, lower alkyl, substituted lower alkyl, aryl or substituted aryl, or —$NR_BR_B$, wherein each $R_B$ is independently selected from hydrogen or lower alkyl, such that when A is —N—, $R_1$ is absent and when B is —N—, $R_3$ is absent;

D is optionally present; and when D is present, D is selected from lower alkylene, substituted lower alkylene, cycloalkylene, substituted cycloalkylene, lower alkenylene, substituted lower alkenylene, or lower alkynylene;

E is optionally present; and when E is present, E is selected from —O—, —C(O)—, —C(O)—$NR_C$—, —C(O)—O—, —O—C(O)—$NR_C$—, —S—, —S(O)—, —S(O)—$NR_C$—, —S(O)$_2$—, —S(O)$_2$—$NR_C$— or —S(O)=NH, wherein $R_C$ is selected from hydrogen, lower alkyl or substituted lower alkyl;

G is optionally present; and when G is present, G is selected from lower alkylene, substituted lower alkylene, lower alkenylene, substituted lower alkenylene or lower alkynylene;

J is a dialkylamino group having the structure J':

—N($R^E$)($R^F$),   (J')

wherein:

$R^E$ and $R^F$ are independently selected from hydrogen, lower alkyl, lower alkenyl, lower alkynyl, lower cycloalkyl and cycloalkyl, or $R^E$ and $R^F$ combine to form a 3–7 membered ring (with 4–6 membered rings being presently preferred), or J is a nitrogen-containing cyclic moiety having the structure J":

as well as bicyclic-derivatives thereof, wherein:

one or both R* can cooperate with one another or with $R_D$ to form further ring(s) or when R* does not cooperate to form a ring, R* is hydrogen, m is 0–2, n is 0–3, X is optionally present, and when present is selected from —O—, —CH$_2$O—, —S—, —CH$_2$S—, —S(O)—, —CH$_2$S(O)—, —S(O)$_2$—, —CH$_2$S(O)$_2$— or —CH$_2$N—, and $R_D$ is selected from hydrogen, lower alkyl or lower cycloalkyl, or $R_D$ is absent when the nitrogen atom to which it is attached participates in the formation of a double bond, with the proviso that when A is —N—, B is —C—, one of $R_2$, $R_3$ or $R_5$ is Cl, D is absent, E is —S— or —O—, and G is alkylene containing 2–4 carbon atoms and J is J'; or when A is —N—, B is —C—, D is absent, G is absent or alkylene containing 1–4 carbon atoms, and J is J", and J" is monocyclic, tropanyl or quinuclidyl, then said modulation does not embrace the control of pain.

Bicyclic derivatives of the above-described nitrogen-containing cyclic moieties include a wide variety of azabicyclic moieties, as described in greater detail herein below.

As employed herein, the phrase "an effective amount", when used in reference to compounds of the invention, refers to doses of compound sufficient to provide circulating concentrations high enough to impart a beneficial effect on the recipient thereof. Such levels typically fall in the range of about 0.001 up to 100 mg/kg/day; with levels in the range of about 0.05 up to 10 mg/kg/day being preferred.

As employed herein, "lower alkyl" refers to straight or branched chain alkyl radicals having in the range of about 1 up to 4 carbon atoms; "alkyl" refers to straight or branched chain alkyl radicals having in the range of about 1 up to 12 carbon atoms; "substituted alkyl" refers to alkyl radicals further bearing one or more substituents such as hydroxy, alkoxy (of a lower alkyl group), mercapto (of a lower alkyl group), aryl, heterocyclic, halogen, trifluoromethyl, pentafluoroethyl, cyano, cyanomethyl, nitro, amino, carboxyl, carbamate, sulfonyl, sulfonamide, and the like;

"lower alkylene" refers to straight or branched chain alkylene radicals (i.e., divalent alkyl moieties, e.g., methylene) having in the range of about 1 up to 4 carbon atoms; "alkylene" refers to straight or branched chain alkylene radicals having in the range of about 1 up to 12 carbon atoms; and "substituted alkylene" refers to alkylene radicals further bearing one or more substituents as set forth above;

"lower cycloalkyl" refers to cyclic radicals containing 3 or 4 carbon atoms, "substituted lower cycloalkyl" refers to lower cycloalkyl radicals further bearing one or more substituents as set forth above, "cycloalkyl" refers to cyclic ring-containing radicals containing in the range of about 3 up to 8 carbon atoms, and "substituted cycloalkyl" refers to cycloalkyl radicals further bearing one or more substituents as set forth above;

"cycloalkylene" refers to cyclic ring-containing divalent radicals containing in the range of about 3 up to 8 carbon atoms (e.g. cyclohexylene), and "substituted cycloalkylene" refers to cycloalkylene radicals further bearing one or more substituents as set forth above;

"lower alkenyl" refers to straight or branched chain hydrocarbyl radicals having at least one carbon-carbon double bond, and having in the range of about 2 up to 4 carbon atoms, and "substituted lower alkenyl" refers to alkenyl radicals further bearing one or more substituents as set forth above;

"alkenyl" refers to straight or branched chain hydrocarbyl radicals having at least one carbon-carbon double bond, and having in the range of about 2 up to 12 carbon atoms (with radicals having in the range of about 2 to 6 carbon atoms presently preferred), and "substituted lower alkenyl" refers to alkenyl radicals further bearing one or more substituents as set forth above;

"lower alkenylene" refers to straight or branched chain alkenylene radicals (i.e., divalent alkenyl moieties, e.g., ethylidene) having at least one carbon-carbon double bond, and having in the range of about 2 up to 4 carbon atoms, and "substituted lower alkenylene" refers to divalent alkenyl radicals further bearing one or more substituents as set forth above;

"alkenylene" refers to straight or branched chain divalent alkenyl moieties having at least one carbon-carbon double bond, and having in the range of about 2 up to 12 carbon atoms (with divalent alkenyl moieties having in the range of about 2 to 6 carbon atoms presently preferred), and "substituted lower alkenylene" refers to divalent alkenyl radicals further bearing one or more substituents as set forth above;

"lower alkynyl" refers to straight or branched chain hydrocarbyl radicals having at least one carbon-carbon triple bond, and having in the range of about 2 up to 4 carbon atoms, and "substituted lower alkynyl" refers to alkynyl radicals further bearing one or more substituents as set forth above;

"alkynyl" refers to straight or branched chain hydrocarbyl radicals having at least one carbon-carbon triple bond, and having in the range of about 2 up to 12 carbon atoms (with radicals having in the range of about 2 up to 6 carbon atoms presently being preferred), and "substituted alkynyl" refers to alkynyl radicals further bearing one or more substituents as set forth above;

"lower alkynylene" refers to straight or branched chain alkynylene radicals (i.e., divalent alkynyl moieties, e.g., ethynylidene) having at least one carbon-carbon triple bond, and having in the range of about 2 up to 4 carbon atoms, and "substituted lower alkynylene" refers to divalent alkynyl radicals further bearing one or more substituents as set forth above;

"alkynylene" refers to straight or branched chain divalent alkynyl moieties having at least one carbon-carbon triple bond, and having in the range of about 2 up to 12 carbon atoms (with divalent alkynyl moieties having in the range of about 2 to 6 carbon atoms presently being preferred), and "substituted alkynylene" refers to divalent alkynyl radicals further bearing one or more substituents as set forth above;

"aryl" refers to aromatic radicals having in the range of 6 up to 14 carbon atoms and "substituted aryl" refers to aryl radicals further bearing one or more substituents as set forth above;

"alkylaryl" refers to alkyl-substituted aryl radicals and "substituted alkylaryl" refers to alkylaryl radicals further bearing one or more substituents as set forth above;

"arylalkyl" refers to aryl-substituted alkyl radicals and "substituted arylalkyl" refers to arylalkyl radicals further bearing one or more substituents as set forth above;

"arylalkenyl" refers to aryl-substituted alkenyl radicals and "substituted arylalkenyl" refers to arylalkynyl radicals further bearing one or more substituents as set forth above;

"arylalkynyl" refers to aryl-substituted alkynyl radicals and "substituted arylalkynyl" refers to arylalkynyl radicals further bearing one or more substituents as set forth above;

"heterocyclic" refers to cyclic (i.e., ring-containing) radicals containing one or more heteroatoms (e.g., N, O, S) as part of the ring structure, and having in the range of 3 up to 14 carbon atoms and "substituted heterocyclic" refers to heterocyclic radicals further bearing one or more substituents as set forth above;

"azabicyclic moieties" refers to fully saturated bicyclic species bearing a nitrogen atom at one of the ring positions, or such moieties may contain one or more sites of unsaturation. Examples of azabicyclic moieties contemplated for use in the practice of the present invention include azabicycloalkanes such as 7-azabicyclo[2.2.1]heptane, N-methyl 7-azabicyclo[2.2.1]heptane, 8-azabicyclo[3.2.1]octane, N-methyl 8-azabicyclo[3.2.1]octane, 1-azabicyclo[2.2.2]octane, N-methyl 1-azabicyclo[2.2.2]octane, 9-azabicyclo[4.2.1]nonane, N-methyl 9-azabicyclo[4.2.1]-nonane, and the like; azabicycloalkenes such as 9-methyl-9-azabicyclo[4.2.1]non-2-ene, and the like. The stereochemistry of azabicyclic moieties includes both endo- and exo- isomers;

"halogen" refers to fluoride, chloride, bromide or iodide radicals.

In accordance with the present invention there are also provided compounds of formula Z as defined hereinabove, excluding compounds wherein:

A is —N—, B is —C—, one of $R_2$, $R_3$ or $R_5$ is Cl, D is absent, E is —S— or —O—, G is alkylene containing 2–4 carbon atoms and J is J', or A is —N—, B is —C—, D is absent, G is absent or alkylene containing 1–4 carbon atoms, J is J'', and J'' is monocyclic, tropanyl or quinuclidyl.

In accordance with the present invention, A and B are independently selected from —N— and —C— with the proviso that one of A and B is —N—. Each of $R_1$ through $R_5$ are independently selected from hydrogen, halogen, cyano, cyanomethyl, nitro, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, heterocyclic, substituted heterocyclic, perfluoro alkyl (such as, for example, trifluoromethyl, pentafluoroethyl, and the like), —$OR_A$, —O—C(O)—$R_A$, —O—C(O)— N($R_A$)$_2$, —$SR_A$, —NHC(O)$R_A$ or —NHSO$_2R_A$, wherein $R_A$ is selected from H, lower alkyl, substituted lower alkyl, aryl or substituted aryl, or —$NR_BR_B$, wherein each $R_B$ is independently selected from hydrogen and lower alkyl.

Preferred compounds are those in which $R_1$ through $R_5$ are each selected from hydrogen, halogen, alkyl, substituted e alkyl (including perfluoroalkyl), alkynyl, substituted alkynyl, —$OR_A$ or —$SR_A$, wherein $R_A$ is selected from H, lower alkyl or aryl, or —$NR_BR_B$, wherein each $R_B$ is independently selected from hydrogen or lower alkyl. More preferably each of $R_1$ through $R_5$ are independently selected from hydrogen, lower alkyl, halogen, hydroxyl, hydroxymethyl, alkoxy, amino, and the like.

In accordance with the present invention, D, when present, is selected from straight chain lower alkylene and substituted lower alkylene moieties, or cycloalkylene and substituted cycloalkylene, or lower alkenylene and substituted alkenylene moieties, or lower alkynylene moieties. It is presently preferred that D not be present, or when present, it is preferred that for D be a lower alkylene chain containing 1 to 3 carbon atoms in the backbone thereof. In particularly preferred compounds of the present invention D is absent or methylene.

Further in accordance with the present invention, E is selected from —O—, —C(O)—, —C(O)O—, —S—, —S(O)—, —S(O)$_2$— or —C(O)NR$_C$—, wherein R$_C$ is selected from hydrogen, lower alkyl or substituted lower alkyl. Preferably E is selected from —O—, —S—, —C(O)O— or —S(O)$_2$—. It is presently especially preferred that E is selected from —S— or —O—.

Still further in accordance with the present invention, G is selected from straight chain lower alkylene and substituted lower alkylene moieties (preferably having up to 3 atoms in the backbone thereof), or lower alkenylene moieties (preferably having about 3 atoms in the backbone thereof), or substituted lower alkenylene moieties and lower alkynylene moieties (preferably having about 3 atoms in the backbone thereof). Presently preferred moieties for G are lower alkylene, of 1 to 3 carbon atoms.

Yet still further in accordance with the present invention, J is a dialkylamino group having the structure (J'):

wherein:
R$^E$ and R$^F$ are independently selected from hydrogen, lower alkyl, lower alkenyl, lower alkynyl, lower cycloalkyl and cycloalkyl, or
R$^E$ and R$^F$ combine to form a 3–7 membered ring (with 4–6 membered rings being presently preferred), or
J is a nitrogen-containing cyclic moiety having the structure(J"):

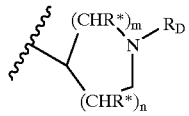

as well as bicyclic-derivatives thereof,
wherein:
one or both R* can cooperate with one another or with R$_D$ to form further ring(s),
m is 0–2,
n is 0–3,
X is optionally present, and when present is selected from —O—, —CH$_2$O—, —S—, —CH$_2$S—, —S(O)—, —CH$_2$S(O)—, —S(O)$_2$—, —CH$_2$S(O)$_2$— or —CH$_2$N—, and
R$_D$ is selected from hydrogen, lower alkyl or lower cycloalkyl, or R$_D$ is absent when the nitrogen atom to which it is attached participates in the formation of a double bond.

Thus, for example, J can be a dialkylamino moiety, an aziridino moiety, azetidino moiety, tetrahydrooxazolo moiety, tetrahydrothiazolo moiety, pyrrolidino moiety, piperidino moiety, morpholino moiety, thiomorpholino moiety, piperazino moiety, an azabicyclic moiety, and the like. Presently preferred compounds include those wherein J is an azetidino moiety, pyrrolidino moiety, 1-methylpyrrolidino moiety, piperidine moiety; 1-methylpiperidine moiety, an azabicyclic moiety (e.g., 7-azabicyclo[2.2.1]heptane, 8-azabicyclo[3.2.1]octane, 1-azabicyclo[2.2.2]octane, 9-azabicyclo[4.2.1]nonane, 9-methyl-9-azabicyclo[4.2.1]non-2-ene), and the like.

Preferred compounds of the present invention include those wherein A and B are independently selected from —N— and —C— with the proviso that one of A and B is —N—, D is lower alkylene or absent; E is as previously defined; G is lower alkylene or lower alkenylene, and J forms a 4-, 5- or 6-membered heterocyclic ring or is an azabicyclic moiety. Particularly preferred compounds of the present invention include those wherein A and B are as defined above, D is methylene or absent, E is —S— or —O—; G is methylene or ethylene; and J is pyrrolidino, 1-methylpyrrolidino, piperidino, 1-methylpiperidino or an azabicyclic moiety.

Additional preferred compounds of the present invention include those wherein E is —C(O)O—; D is lower alkylene; G is lower alkylene; and J is pyrrolidino, 1-methylpyrrolidino, piperidino, 1-methylpiperidino or an azabicyclic moiety.

Additional preferred compounds of the invention include those wherein E is —S—; D is not present; G is methylene or ethylene; J is pyrrolidino, 1-methylpyrrolidino, piperidino, 1-methylpiperidino or an azabicyclic moiety.

Additional preferred compounds of the invention include those wherein E is —O—; D is methylene or not present; G is methylene; J is pyrrolidino, 1-methylpyrrolidino, piperidino, 1-methylpiperidino or an azabicyclic moiety.

Additional preferred compounds of the invention include those wherein E is —S—; D is methylene or not present; G is methylene; and at least one of R$^1$, R$^2$, R$^3$, R$^4$ or R$^5$ is not hydrogen.

Additional preferred compounds of the invention include those wherein E is —S—; neither D nor G are present; J is pyrrolidino, piperidino or azabicyclic moiety; as well as compounds wherein E is —S—; D is not present; G is methylene; and J is an azabicyclic moiety.

Additional preferred compounds of the invention include those wherein E is —S—; D is not present; G is —(CH$_2$)$_n$—, wherein n=1–6, e.g., methylene, ethylene, propylene, butylene, and the like; and J is dialkylamino (e.g., dimethylamino), pyrrolidino, piperidino, or an azabicyclic moiety.

Invention compounds have affinity for acetylcholine receptors. As employed herein, the term "acetylcholine receptor" refers to both nicotinic and muscarinic acetylcholine receptors. Affinity of invention compounds for such receptors can be demonstrated in a variety of ways, e.g., via competitive radioligand binding experiments in which the test compounds displace isotopically labeled ligands (such as nicotine, cytisine, methylcarbamylcholine, quinuclidinyl benzilate, and the like) from binding sites in mammalian cerebral membranes (see, e.g., Example 35). Furthermore, the binding of compounds to acetylcholine receptors can be evaluated as a functional response (see, e.g., Example 37).

For example, the activity of invention compounds can be evaluated employing functional assays based on recombinant neuronal acetylcholine receptor expression systems (see, for example, Williams et al., *Drug News & Perspectives* 7:205–223 (1994)). Test compounds can also be evaluated for their ability to modulate the release of neurotransmitters (e.g., dopamine, norepinephrine, and the like) from rat brain slices (e.g., striatum, hippocampus, and the like). See, e.g., Example 36.

Moreover, test compounds can also be evaluated by way of behavioral studies employing animal models of various CNS, autonomic and cardiovascular disorders (see, for example, D'Amour and Smith, *J. Pharmacol. Exp. Ther.* 72:74–79 (1941) and Iwamoto, *J. Pharmacol. Exp. Ther.* 251:412–421 (1989) for animal models of pain; Klockgether and Turski, *Ann. Neurol.* 28:539–546 (1990), Colpaert, F., *Neuropharmacology* 26:1431–1440 (1987), Ungerstedt and Arbuthknott, *Brain Res.* 24:485–493 (1970), Von Voigtlander and Moore, *Neuropharmacology* 12:451–462 (1973), Ungerstedt et al., *Adv. Neurol.* 3:257–279 (1973), Albanese et al., *Neuroscience* 55:823–832 (1993), Janson et al., *Clin. Investig.* 70:232–238 (1992), Sundstrom et al., *Brain Res.* 528:181–188 (1990), Sershen et al., *Pharmacol. Biochem. Behav.* 28:299–303 (1987) for animal models of Parkinson's disease; Williams et al., *Gastroenterology* 94:611–621 (1988), Miyata et al., *J. Pharmacol. Exp. Ther.* 261:297–303 (1992), Yamada et al., *Jpn. J. Pharmacol.* 58 (Suppl.):131 (1992) for animal models of irritable bowel syndrome; Coyle et al., *Neurobehav. Toxicol. Tetatol.* 5:617–624 (1983), Schartz et al., *Science* 219:316–318 (1983) for animal models of Huntington's disease; Clow et al., *Euro. J. Pharmacol.* 57:365–375 (1979), Christensen et al., *Psychoparmacol.* 48:1–6 (1976), Rupniak et al., *Psychopharmacol.* 79:226–230 (1983), Waddington et al., *Science* 220:530–532 (1983) for animal models of tardive dyskinesia; Emerich et al., *Pharmacol. Biochem. Behav.* 38:875–880 (1991) for animal models of Gilles de la Tourette's syndrome; Brioni et al., *Eur. J. Pharmacol.* 238:1–8 (1993), Pellow et al., *J. Neurosci. Meth.* 14:149 (1985) for animal models of anxiety; and Estrella et al., *Br. J. Pharmacol* 93:759–768 (1988) for the rat phrenic nerve model which indicates whether a compound has muscle effects that may be useful in treating neuromuscular disorders).

Those of skill in the art recognize that invention compounds may contain one or more chiral centers, and thus can exist as racemic mixtures. For many applications, it is preferred to carry out stereoselective syntheses and/or to subject the reaction product to appropriate purification steps so as to produce substantially optically pure materials. Suitable stereoselective synthetic procedures for producing optically pure materials are well known in the art, as are procedures for purifying racemic mixtures into optically pure fractions.

In the following reaction Schemes, each of A, B, D, E, G and J are as defined above. When any one or more of the R-group substituents (i.e., $R_1$, $R_2$, $R_3$, $R_4$ or $R_5$) are —OH or —SH, it will be readily apparent to those of skill in the art that this functional group.may require the use of "protecting groups" (e.g., t-butyldimethylsilyl (t-BDMS), benzyl ($B_n$) or tetrahydrophenyl (THP), and the like) during the coupling reaction to "block" the reactivity of the R group. Similarly, when the R-group is —$NH_2$, protecting groups (e.g., 9-fluoromethylcarbonyl (FMOC), butoxycarbonyl (BOC), benzoyloxycarbonyl (CBZ), and the like) may be required. Furthermore, when J=pyrrolidine, an additional protecting step may be required. For such purpose, BOC, CBZ, and the like can be employed. Hence, subsequent deprotection will be required prior to analysis.

A variety of methods can be employed for the preparation of compounds having the general formula Z. For example, an example scheme for the production of compounds wherein E represents a sulfur linking moiety are shown in Reaction Schemes I and II.

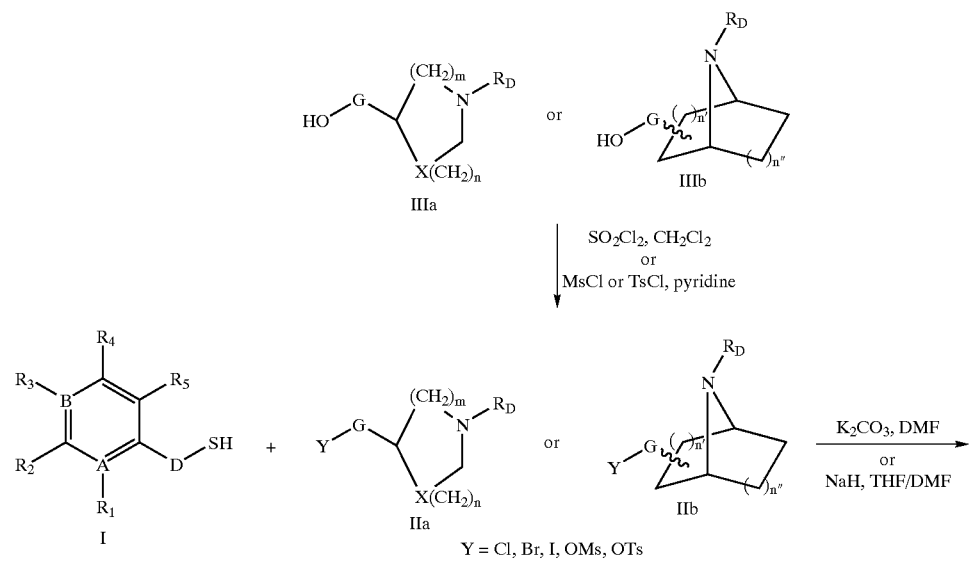

Reaction Scheme I

-continued

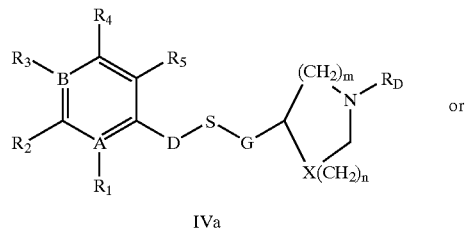

IVa

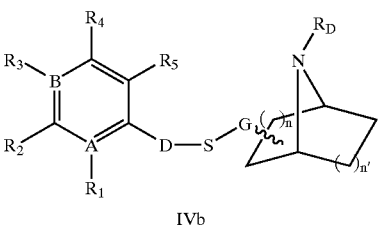

IVb

All variables used in the schemes presented herein are as defined above, and n' and n" each fall within the range of 1–3.

In reaction Scheme I the sulfhydryl derivatives, (compounds I) are commercially available (e.g., 2-mercaptopyridine, 4-mercaptopyridine, Aldrich Chemical Co., 2-pyridinemethanethiol, Pyrazine Specialties Inc.) or may readily be prepared by those skilled in the art by selecting the appropriate D moiety (e.g., 2-pyridinemethanethiol, 2-pyridineethanethiol, Barnes, J. H. et al., *Eur. J. Med. Chem.* 23:211 (1988)).

Alternatively, the sodium or lithium salt of I can be used to produce compounds of general Formula IVa or IVb. In this case no base is needed and the reaction can be conducted in a solvent such as methanol or ethanol. Reaction times required for this coupling procedure can vary widely and fall in the range of 10 minutes up to about 24 hours. Preferred reaction times fall in the range of about one hour. This reaction can be carried out over a wide range of temperatures. Temperatures in the range of room temperature are presently preferred.

In Reaction Scheme I, the sulfur compounds (compounds I) are effectively contacted with halides or their equivalents, especially chloride or mesylate derivatives (compounds IIa or IIb), optionally bearing G. Compounds IIa or IIb are commercially available (e.g., 2-(2-chloroethyl)-1-methylpyrrolidine, Aldrich Chemical Co.) or may be prepared from starting materials well-known to those skilled in the art (see e.g., Wrobel and Hejchman, *Synthesis* 5:452 (1987) or Gautier et al., *Ann. Pharm. Fr.* 30:715 (1972)) or, alternatively, the mesylate derivative or the chloro derivative may also be prepared from the corresponding alcohol (compound IIIa or IIIb), according, respectively, to Fürst and Koller, *Helv. Chim. Acta* 30:1454 (1947) and Tabushi, I., *Tetrahedron Lett.* 293 (1970). The alcohol derivatives are commercially available (e.g., tropinone, Aldrich Chemical Co.), may be prepared (e.g., endo-7-methyl-7-azabicyclo[2.2.1]heptane-2-ol, Pfister, J. R. et al., *J. Pharm. Sci.* 74:108 (1985); endo-7-azabicyclo[2.2.1]heptane-2-ol, Fletcher,J.,*J. Org. Chem.* 59:1771 (1994); exo or endo-9-methyl-9-azabicyclo[4.2.1]nonane, Campell, H. F. et al., *Can. Pol. J. Chem.* 53:27 (1979) or can be obtained by reduction of the corresponding ester using methods well-known to those skilled in the art (e.g., 6-carboxylic acid-8-methyl-8-azabicyclo[3.2.1]octane-methylester, Gonzalez at al., *J. Am. Chem.* 117:3405 (1995)). Similarly, chloro, mesylate or tosylate derivatives of dialkylamines can be used instead of compounds of Formula IIa or IIb. This coupling reaction is promoted by suitable base, such as, for example potassium hydroxide, sodium hydride, sodium ethoxide, potassium carbonate, 1,8-diazatribyclo[5.4.0]undec-7-ene (DBU), and the like. Presently preferred base for use in the practice of the present invention is potassium carbonate or sodium hydride. The above-described reaction is typically carried out in a solvent such as methanol, tetrahydrofuran (THF), dimethylformamide (DMF), and the like. Presently preferred solvent for use in the practice of the present invention is DMF or a 50/50 mixture of THF and DMF.

Typically the coupling reaction can be carried out over a wide range of temperatures. Temperatures in the range of room temperature to 80° C. are presently preferred. Reaction times required to effect the desired coupling reaction can vary widely, typically falling in the range of 10 minutes up to about 24 hours. Preferred reaction times fall in the range of about 30 minutes to 12 hours. The resulting thioether derivative may be purified and analyzed by techniques well known to those skilled in the art.

Alternatively, compounds of Formula IVa or IVb may be prepared following the reaction described in Reaction Scheme II.

Reaction Scheme II

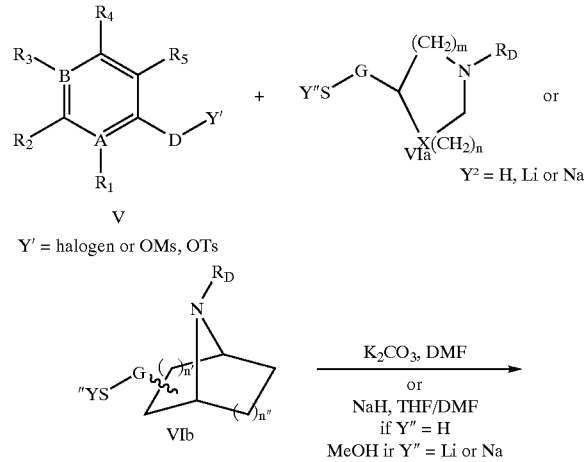

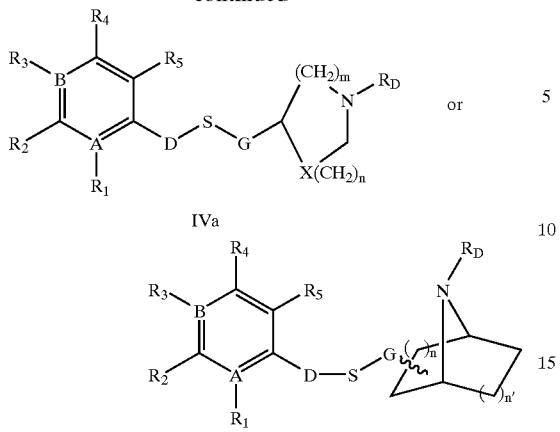

In Reaction Scheme II, compound of formula V (wherein D is selected from methylene or ethylene unit and Y' is halogen, a mesylate or a tosylate group) are commercially available or may be readily prepared from starting materials well-known to those skilled in the art. Compounds VIa or VIb can be prepared according to Reaction Scheme III from the corresponding compound of general formula IIa or IIb. When Y" is hydrogen, the coupling reaction is promoted by suitable base, such as, for example potassium hydroxide, sodium hydride, sodium ethoxide, potassium carbonate, 1,8-diazabicyclo[5.4.0]undec-7-ene (DBU), and the like. Presently preferred base for use in the practice of the present invention is potassium carbonate or sodium hydride.

The above-described reaction is typically carried out in a solvent such as methanol, THF, DMF, and the like. Presently preferred solvent for use in the practice of the present invention is DMF or a 50/50 mixture of THF and DMF.

When Y" is a sodium or lithium cation, the coupling reaction is conducted directly after the hydrolysis of the thioacetate (Scheme III) in the same solvent (methanol) in a one pot reaction by addition of one equivalent of compound of general Formula V.

A method for the preparation of compounds of general Formula VIa or VIb is depicted in Scheme III.

Reaction Scheme III

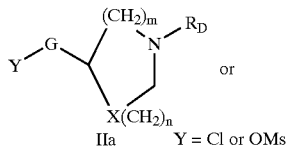

In Step A of reaction Scheme III, compound of general formula IIa or IIb is contacted with potassium thioacetate, via a nucleophilic substitution well known to those skilled in the art in order to obtain the thioacetate of general Formula VIIa or VIIb.

In Step B of the reaction Scheme III, the resulting thioesters (compound VIIa or VIIb) are hydrolyzed using procedures well know to those of skill in the art, such as litium hydroxide in methanol, sodium methoxide in methanol and the like, to provide the desired thiol derivative of general formula VIa or Vib.

Exemplary methods for the preparation of compounds having the general Formula Z, as described hereinabove, wherein E represents a sulfoxide linking moiety (—S(O)—) or a sulfone linking moiety (—S(O)$_2$—), are shown in reaction Scheme IV.

Reaction Scheme IV

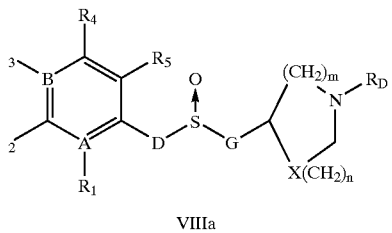
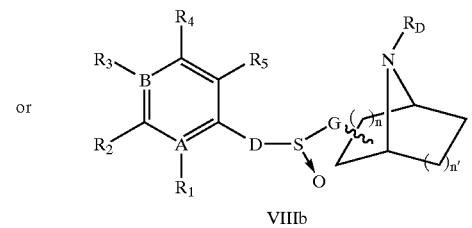

↑ Step A

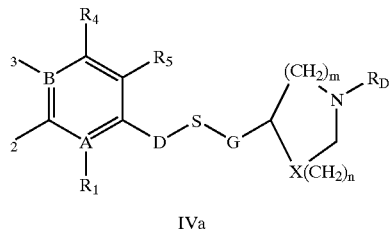

IVa or

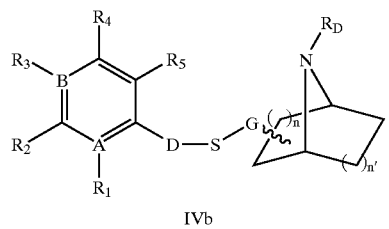

IVb

↓ Step B

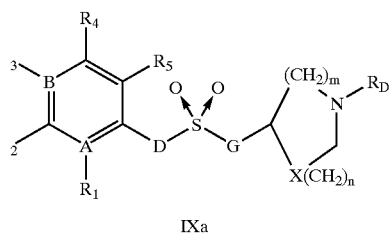

IXa or

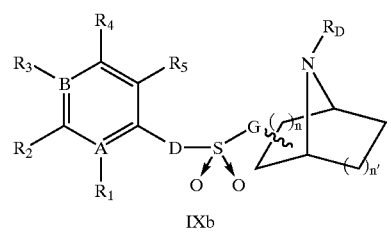

IXb

In step A, the resulting thioether derivatives produced, for example, as described in Reaction Scheme I or II (compounds IVa or IVb), may be oxidized to their corresponding sulfoxides (compounds VIIIa or VIIIb) using about one to about five equivalents of a suitable oxidant, such as, for example, hydrogen peroxide or a hydrogen peroxide derivative such as tert-butyl hydroperoxide, peracids (such as 3-chloroperbenzoic acid), halogen oxide derivatives (such as sodium metaperiodate), N-halogenated derivatives (such as N-bromo or N-chlorosuccidimide), and the like (for a review see Madesclaire, M., *Tetrahedron* 42:5459 (1985)). Presently preferred oxidant for use in the practice of the present invention is about three equivalents of hydrogen peroxide. The above-described reaction is typically carried out in a solvent such as methylene chloride, acetic acid, dioxane, ethanol, methanol, and the like. Presently preferred solvent for use in the practice of the present invention is acetic acid.

Typically the reaction can be carried out over a wide range of temperatures, typically falling in the range of about −78° C. up to reflux. Temperatures in the range of about 22° C. are presently preferred. Reaction times required to effect the desired oxidation reaction can vary widely, typically falling in the range of 10 minutes up to about 24 hours. Preferred reaction times fall in the range of about 30 minutes to one hour. The resulting sulfoxides (compound VIIIa or VIIIb) may be purified and analyzed by techniques well known to those skilled in the art.

Alternatively, in step B of Reaction Scheme IV, the thioether derivatives (compounds IVa or IVb) may be oxidized to their corresponding sulfones (compounds IXa or IXb) using procedures similar to those described above for preparing sulfoxides, but employing elevated levels of oxidant and/or elevated reaction temperatures. In the present invention, hydrogen peroxide in acetic acid under reflux is the preferred condition (R. Gaul et al., *J. Org. Chem.* 26:5103 (1961)). The resulting sulfones (compounds IXa or IXb) are purified and analyzed by techniques well known to those skilled in the art.

Exemplary methods for the preparation of compounds having the general Formula Z, as described hereinabove, wherein E is represents an ester linking moiety (i.e., —C(O)O—), are shown in Reaction Schemes V and VI. In Reaction Scheme V, compounds of Formula X, wherein D is absent or selected from methylene or ethylene, are commercially available and are well known to those skilled in the art. Those compounds not currently available may readily be prepared from starting materials well-known to those skilled in the art.

Reaction Scheme V

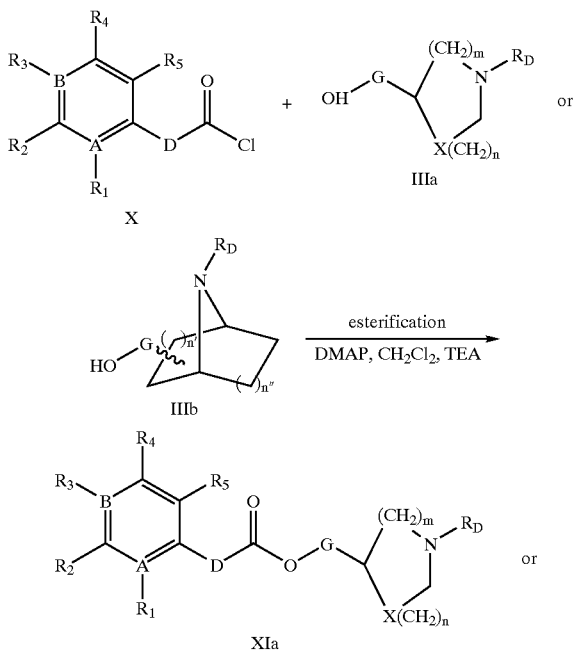

-continued

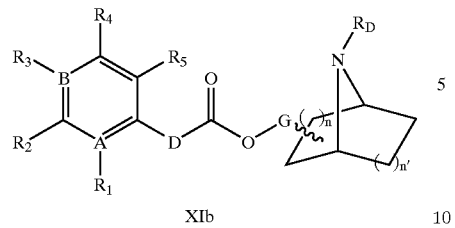

XIb

-continued

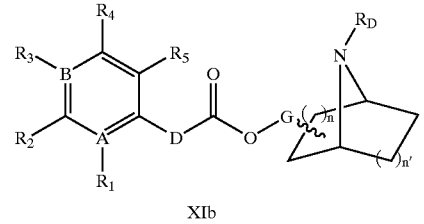

XIb

In Reaction Scheme V, the aryl acid chlorides of Formula X are effectively contacted with the primary alcohol compounds of Formula IIIa or IIIb, optionally bearing G, and a base such as dimethylaminopyridine (DMAP) under anhydrous conditions in an aprotic solvent, such as, for example, methylene chloride ($CH_2Cl_2$), tetrahydrofuran (THF), diethyl ether, benzene, toluene, and the like. Compounds of Formula IIIa or IIIb are described in Scheme I. Similarly, hydroxy derivatives of dialkylamines can be used instead of compounds of Formula IIIa or IIIb. The reaction mixtures are stirred for 1 to 16 hr, with 4 hours preferred, at reaction temperatures within the range of −78° C. up to reflux, with ambient temperatures presently preferred. The resulting esters (Formula XIa or XIb) are typically purified and analyzed by techniques well known to those of skill in the art.

Further, compounds of Formula XIa or XIb may be prepared from aryl carboxylic acid derivatives according to Reaction Scheme VI.

Carboxylic acid derivatives XII employed in Reaction Scheme VI are commercially available or may readily be prepared from well-known starting materials. Compounds of Formula XII are coupled with compounds of Formula IIIa or IIIb in the presence of triethylamine (TEA), 1-(3-dimethylaminopropyl)-3-ethylcarbodiimide (EDC) in an aprotic solvent such as methylene chloride ($CH_2Cl_2$) or chloroform and the like. Similarly, hydroxy derivatives of dialkylamines can be used instead of compounds of Formula IIIa or IIIb. The reaction mixtures are stirred for 8 to 16 hr, with 12 hr preferred, at reaction temperatures within the range of −78° C. to reflux, with ambient temperatures presently preferred, to afford compounds XIa or XIb. The resulting esters are typically purified and analyzed by techniques well known to those of skill in the art.

Exemplary methods for the preparation of compounds having the general Formula Z, as described hereinabove, wherein D is present or absent and G is a lower alkenylene, are shown in reaction Scheme VII.

Reaction Scheme VI

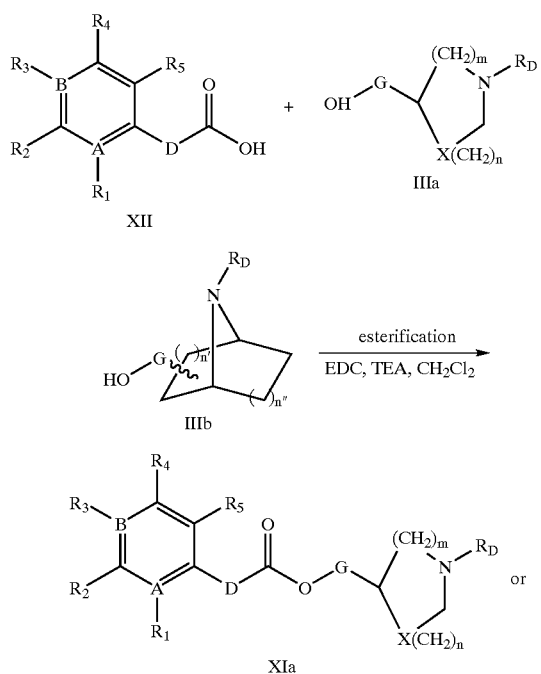

Reaction Scheme VII

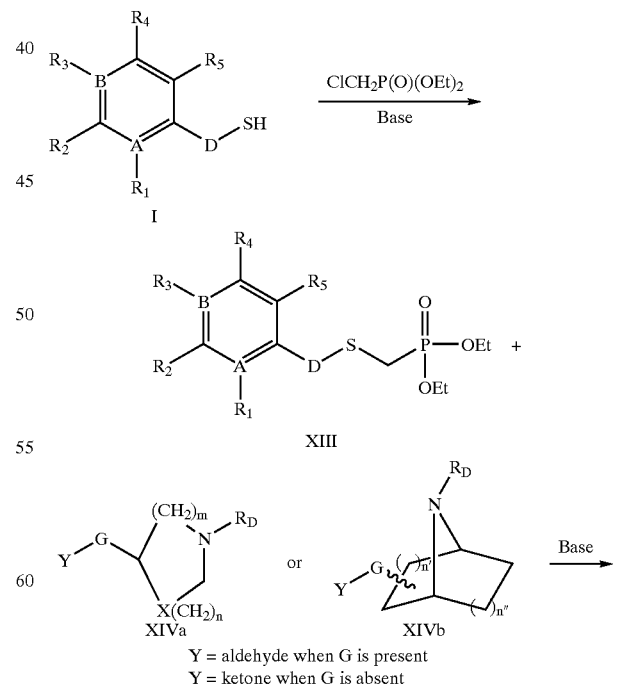

Y = aldehyde when G is present
Y = ketone when G is absent

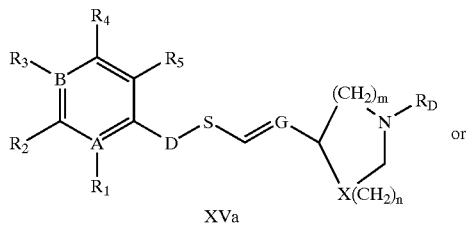

XVa

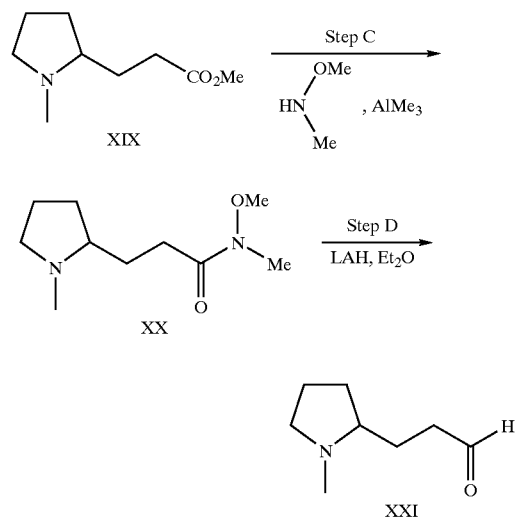

As illustrated in Reaction Scheme VII, thio derivatives I (see Scheme I) are reacted with diethyl chloromethylphosphonate. The reaction is promoted by a suitable base, such as, for example potassium carbonate, sodium hydroxide, sodium ethoxide, sodium hydride and the like in a suitable solvent such as, methanol, ethanol, DMF.

Presently preferred base for use in the practice of the present invention is potassium carbonate in dimethylformamide (DMF). Typically this reaction may be carried out over a wide range of temperature. Temperatures in the range of 0° C. to room temperature are presently preferred. Reaction time required to effect the desired reaction can vary widely, typically falling in the range of 10 minutes up to about 24 hours. In the second step compound XIII reacts with the aldehyde or the ketone XIVa or XIVb under Wittig-Horner olefination conditions, well-known to those skilled in the art, to form the olefin XVa or XVb. Compounds XIVa or XIVb are commercially available (e.g., 8-methyl-8-azabicyclo [3.2.1]octane-3-one, Aldrich Chemical Co.), may be prepared from starting materials well-know to those skilled in the art (e.g., 9-methyl-9-azabicyclo[4.2.1]nonane-2-one; Wiseman, J. et al., *J. Org. Chem.* 2485:13 (1985); 8-methyl-8-azabicyclo[3.2.1]octane-6-one, Aaron, H. S. et al., J. Heterocycl. Chem. 423:5 (1968)) or may be prepared according to Scheme VIII.

A method for the preparation of compounds of Formula XIV is depicted in Scheme VIII.

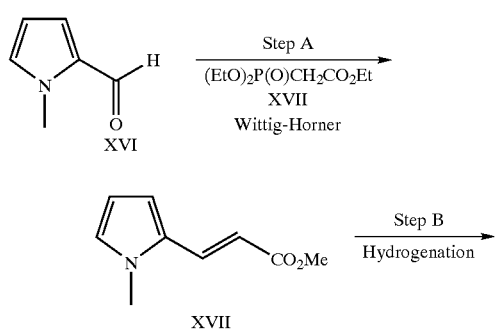

In step A of reaction Scheme VIII, aldehyde XVI is contacted with triethyl phosphonoacetate XVII, via a Wittig-Horner reaction well known to those skilled in the art in order to obtain the unsaturated ester (compound XVIII).

In step B of reaction Scheme VIII the resulting unsaturated ester (compound XVIII) may be reduced to the corresponding saturated ester (compound XIX) using procedures well known to those skilled in the art, such as catalytic hydrogenation using a pressure of hydrogen, a catalyst such as $PtO_2$ and a solvent such as acetic acid, ethanol, methanol, and the like.

In step C of reaction Scheme VIII the saturated ester (compound XIX) is contacted with N-methoxy-N-methylamine in the presence of trimethylaluminium in an aprotic solvent such as benzene in order to form the corresponding Weinreb amide (compound XX) (Levin et al., *Synt. Com.* 12:989 (1982)). Alternatively the ester (compound XIX) can be transformed to the corresponding acyl chloride and transformed to the Weinred amide using condition well known to those skilled in the art (Weinred et al. Tetrahedron Lett 22:3815 (19871)).

In step D of reaction Scheme VIII compound XX may be reduced to the aldehyde (compound XXI) using procedures well know to those skilled in the art, such as lithium aluminium hydride in ether or tetrahydrofuran (THF).

Similarly, aldehyde derivatives of dialkylamines or azabicycloalkanes can be synthesized using the same type of methodology.

Exemplary methods for the preparation of compounds having the general Formula Z, as described hereinabove, wherein E is not present, are shown in Reaction Scheme IX.

Reaction Scheme IX

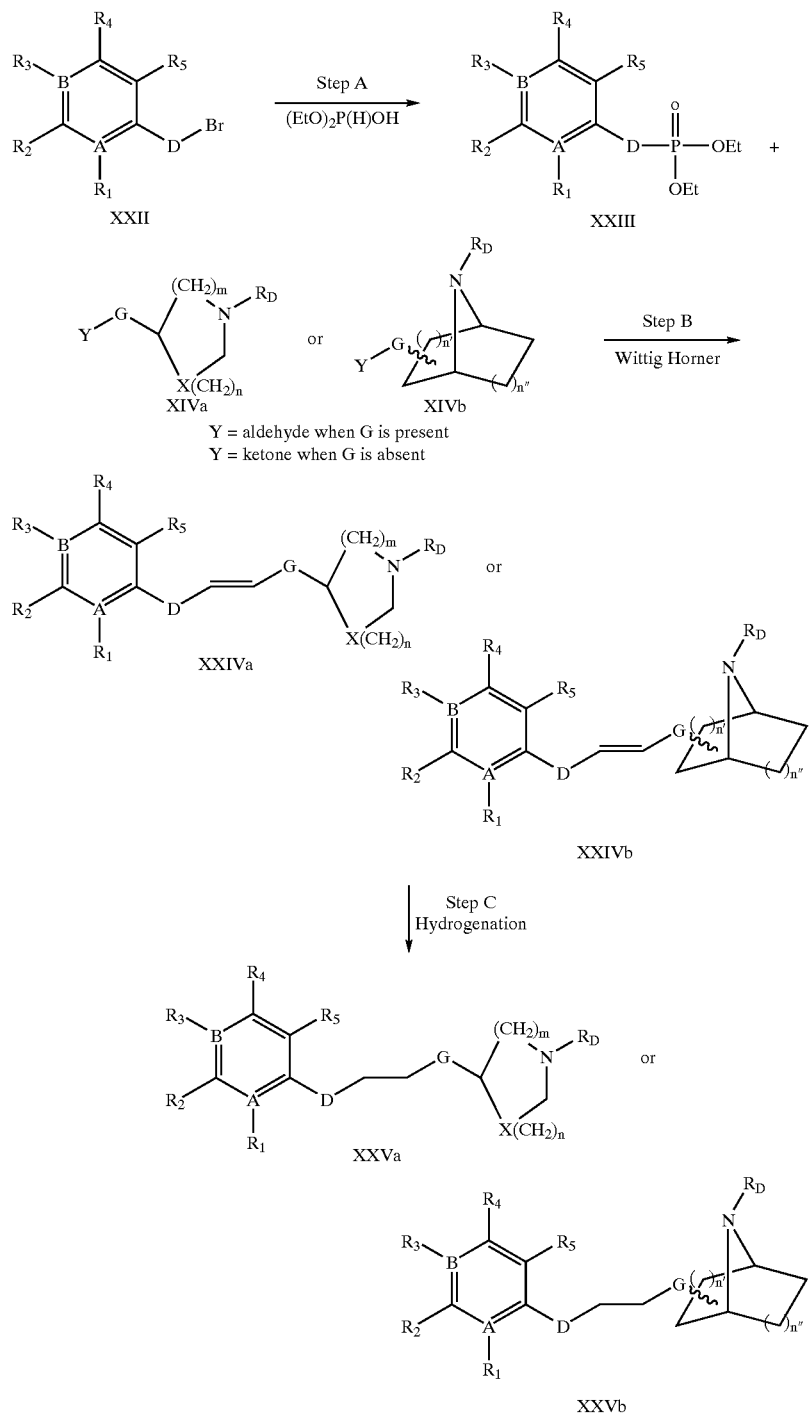

As illustrated in Reaction Scheme IX, halogenated derivatives (compounds XXII), are reacted with diethyl phosphite in an aprotic solvent such as benzene, toluene, acetonitrile, tetrahydrofuran and the like in the presence of a base such as, sodium hydride, butyl lithium, forming the corresponding Wittig-Horner reagent (compounds XXIII). Typically this reaction may be carried out over a wide range of temperatures. Temperatures in the range of about 0° C. are presently preferred. Reaction times required to effect the desired coupling reaction can vary widely, typically falling in the range of 10 minutes up to about 24 hours. Preferred reaction times fall in the range of 1 hour. The resulting compounds may be purified and analyzed by techniques well known to those skilled in the art.

In Step B of Reaction Scheme IX, the Wittig-Horner reagent (compounds XXIII) are alternatively contacted with an appropriate aldehyde or ketone (compounds XIVa or XIVb; see Scheme VII), via a Wittig-Horner reaction well-known to those skilled in the art to afford compounds XXIVa or XXIVb.

In Step C of Reaction Scheme XIV, the resulting alkenylene-linker derivatives (compounds XXIVa or XXIVb) may be reduced to their corresponding saturated alkylene derivatives (compounds XXVa or XXVb) using procedures well known to those of skill in the art, such as exposure to hydrogen using a Pd/C catalyst.

Similiary derivatives of dialkylamines can be synthesized using the same type of methodology.

Exemplary methods for the preparation of compounds having the general formula Z, as described hereinabove, wherein E is represents an oxygen linking moiety are shown in Reaction Scheme X.

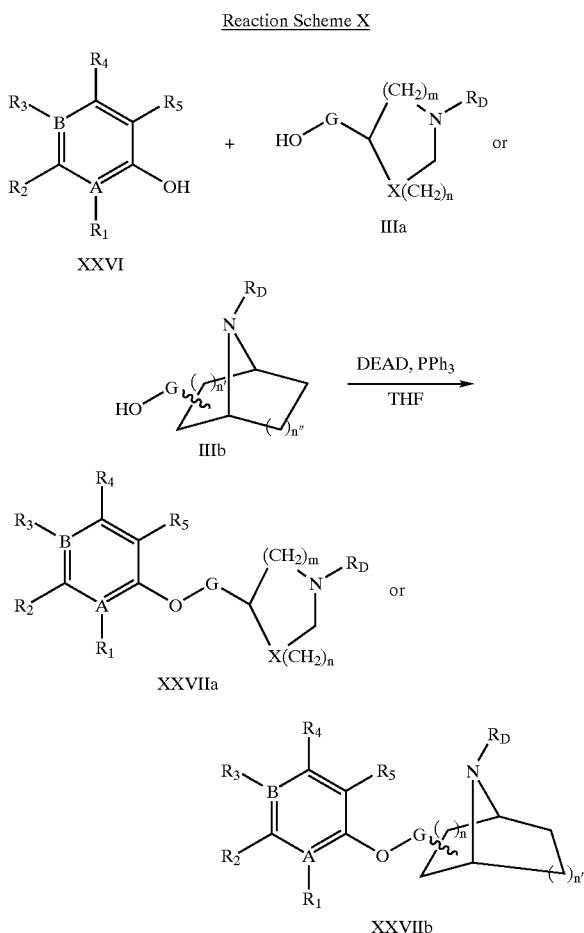

In Reaction Scheme X hydroxypyridine derivatives (compound XXVI) are commercially available (e.g., 2-hydroxypyridine, 4-hydroxypyridine, Aldrich Chemical Co.). Compounds of Formula IIIa and IIIb are described in Scheme I. Mitsunobu's conditions can be used to obtain the desired compound. This reaction is promoted by diethyl azodicarboxylate or diisopropyl azodicarboxylate in the presence of a phosphine such as triphenylphosphine, tributylphosphine and the like. Presently diethyl azodicarboxylate and triphenylphosphine are preferred. The above-described reaction is typically carried out in an aprotic solvent such as tetrahydrofuran(THF), ether, benzene, toluene, acetonitrile and the like. Presently preferred solvent for the use in the practice of the present invention is tetrahydrofuran(THF). Typically the reaction can be carried out over a wide range of temperatures, usually in the range of about −78° C., up to reflux. Temperatures in the range of 22° C., are presently preferred. The resulting ether (compounds XXVIIa and XVIIb) may be purified and analyzed by techniques well known to those skilled in the art.

In accordance with another embodiment of the present invention, there are provided pharmaceutical compositions comprising substituted pyridine compounds as described above, in combination with pharmaceutically acceptable carriers. Optionally, invention compounds can be converted into non-toxic acid addition salts, depending on the substituents thereon. Thus, the above-described compounds (optionally in combination with pharmaceutically acceptable carriers) can be used in the manufacture of a medicament for modulating the activity of acetylcholine receptors.

Pharmaceutically acceptable carriers contemplated for use in the practice of the present invention include carriers suitable for oral, intravenous, subcutaneous, transcutaneous, intramuscular, intracutaneous, inhalation, and the like administration. Administration in the form of creams, lotions, tablets, dispersible powders, granules, syrups, elixirs, sterile aqueous or non-aqueous solutions, suspensions or emulsions, patches, and the like, is contemplated. Also contemplated is single dose administration, sustained release administration (e.g., employing time release formulations, metered delivery, repetitive administration, continuous delivery, and the like), administration in combination with other active ingredients, and the like.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use.

Invention compounds can optionally be converted into non-toxic acid addition salts. Such salts are generally prepared by reacting the compounds of this invention with a suitable organic or inorganic acid. Representative salts include the hydrochloride, hydrobromide, sulfate, bisulfate, methanesulfonate, acetate, oxalate, valerate, oleate, laurate, borate, benzoate, lactate, phosphate, tosylate, citrate, maleate, fumarate, succinate, tartrate, napsylate, and the like. Such salts can readily be prepared employing methods well known in the art.

The invention will now be described in greater detail with reference to the following non-limiting examples. All references cited herein are hereby incorporated by reference.

EXAMPLE 1

Synthesis of Invention Thioether Compounds IVa or IVb Synthetic Scheme I or Scheme II Method A):

Into a two neck flask fitted with a condenser, a thermometer and flushed with argon was placed compound of general Formula II and compound of general Formula I (Scheme I) or compound of general Formula VI and compound of general Formula V (Scheme II), potassium carbonate (3 eq) and dry dimethylformamide (3 mL/mmol). The reaction mixture was either stirred at room temperature overnight or heated at 70° C. for 30 min. The mixture was filtered through celite to remove excess potassium carbonate, hydrolyzed (5 mL/mmol) and extracted three times with ethyl acetate (4 mL/mmol). The organic layer were combined, washed with brine (3×5 mL/mmol), dried (MgSO$_4$) and concentrated under vacuum (15 mm Hg) to give an oil. The crude material was purified via chromatography on silica using a gradient of chloroform and methanol as eluant. The pure compound of general Formula IV was converted to the HCl salt.

EXAMPLE 2

Formation of Thioether of
General Formula IVA or IVb

Method B:

Into a three neck flask fitted with a condenser, an addition funnel, a thermometer and flushed with argon was placed sodium hydride (1.1 eq) and THF (1.5 mL/mmol). The thiol derivative of general Formula I (Scheme I) or general Formula VI (Scheme II) (1 eq) previously dissolved in THF (0.5 mL/mmol) was added dropwise at 0° C. After the addition was completed the reaction mixture was allowed to stir at this temperature for 15 min and compound of general Formula II (Scheme I) or general Formula V (Scheme II) (1 eq) previously dissolved in dry DMF (2 mL/mmol) was added dropwise. The mixture was allowed to warm up to room temperature, heated at 70° C. for 1.5 hours, cooled to room temperature and stirred overnight. After hydrolysis with water (5 mL/mmol) and extraction three times with EtOAc (5 mL/mmol), the organic layers were combined, washed with brine (3×5 mL/mmol), dried (MgSO4) and concentrated under vacuum (15 mm Hg) to give an oil. The crude material was purified via chromatography on silica using a gradient of chloroform and methanol as eluant. The resulting pure compound of general Formula IV was converted to the HCl salt.

EXAMPLE 3

Formation of Thioether of
General Formula Iva or IVb

Method C:

The sodium or lithium salt of compound of general Formula I (Scheme I) or general Formula VI (Scheme II) (obtained by hydrolysis with a normal aqueous solution of LiOH (30 min to 1 hour; 1 eq) of the corresponding thioacetate (see method D)) and one equivalent of compound of general Formula II (Scheme I) or general Formula V (Scheme II) were mixed together in methanol (2 mL/mmol). The reaction mixture was stirred at room temperature and monitored by TLC until completion. The solvent was removed under vacuum. Water was added to the residue and the mixture was extracted three times with EtOAc (4 mL/mmol). The organic layers were combined, washed with brine (5 mL/mmol), dried (MgSO$_4$) and concentrated under vacuum (15 mm Hg) to give an oil. The crude material was purified via chromatography on silica using a gradient of chloroform and methanol as eluant. The resulting pure compound of general Formula IV was converted to the HCl salt.

EXAMPLE 4

Formation of Thioether of
General Formula Iva or IVb

Method D:

a) Formation of the thioacetate:

Into a two neck flask fitted with a condenser, a thermometer and flushed with argon was placed the halide or mesylate derivative of general Formula II (1 eq) or general formula V, potassium thioacetate (1.2 eq), dry dimethylformamide (DMF) (1.5 mL/mmol) or dry methylene chloride containing about 10 to 20% of DMF and a base such as potassium carbonate (3 eq) or diisopropylethyl amine (1.5 eq). The reaction mixture was stirred at room temperature and monitored by TLC until completion. In general the reaction is complete after 2 to 3 hours (some compounds require 30 min at 70° C.) The mixture was hydrolyzed and extracted three times with ethyl acetate (4 mL/mmol). The organic layers were combined, washed with brine (3×5 mL/mmol), dried (MgSO$_4$) and concentrated under reduced pressure (15 mm Hg). The resulting oil was purified via flash chromatography on silica using a gradient of choroform and methanol to provide the desired thioacetate.

b) hydrolysis of the thioacetate:

The resulting thioacetate is hydrolyzed using sodium hydroxide (1.1 eq) or lithium hydroxide (1.1 eq) in methanol (1.5 mL/mmole). In general the reaction is complete in 30 min. The solvent is removed under vacuum (15 mm Hg) and water was added. The pH is adjusted to 6–7 by addition of HCl (1N) and the aqueous solution is extracted three times with EtOAc (4 mL/mmol). The organic layers are combined, washed with brine (5 mL/mmol), dried (MgSO$_4$) and concentrated under vacuum (15 mm Hg) to produce the desired thiol-derivative in high yield.

EXAMPLE 5

2-[2-(4-Pyridine)thioethyl]-1-methylpyrrolidine
Method A)

2-(2-chloroethyl)-1-methylpyrrolidine (4.99 g, 27.0 mmol), 4-mercaptopyridine (3.0 g; 27.0 mmol), potassium carbonate (11.19 g, 80.96 mmol) and DMF (80 mL) were combined and stirred at room temperature for 2 days, yielding 2.96 g (13.3 mmol, 49%) of the desired compound which was converted to the hydrochloride salt. $^1$H NMR (300 MHz, CD$_3$OD) δ 8.56 (d, J=7 Hz, 2H), 7.96 (d, J=7 Hz, 2H), 3.72 (m, 1H), 3.58 (m, 1H), 3.41 (m, 2H), 3.20 (m, 2H), 22.96 (s, 3H), 2.48 (m, 1H), 2.14 (m, 3H), 1.93 (m, 1H); $^{13}$C (75.5 MHz, CD$_3$OD) δ 165.9, 140.9, 123.8, 69.3, 57.5, 40.2, 30.6, 30.2, 28.8, 22.7; mp 186.5–187.5° C.; C H N Analysis C$_{12}$H$_{18}$N$_2$S.2.5HCl.

EXAMPLE 6

2-[2-(2-Pyridine)thioethyl]-1-methylpyrrolidine
(Method B)

2-(2-chloroethyl)-1-methylpyrrolidine (6.64 g, 45.0 mmol), 2-mercaptopyridine (5.0 g; 45.0 mmol), sodium hydride (1.62 g, 67.47 mmol) gave to 7.03 g (31.6 mmol, 85%) of the desired compound which was converted to the hydrochloride salt. $^1$H NMR (300 MHz, CD$_3$OD) δ 8.72 (d, J=7 Hz, 1H), 8.49 (t, J=7 Hz, 1H), 8.13 (d, J=7 Hz, 1H), 7.18 (t, J=7 Hz, 1H), 3.8 (m, 1H), 3.6 (m, 2H), 3.25 (m, 1H), 3.03 (s, 3H), 2.55 (m, 1H), 2.2 (m, 3H), 2.0 (m, 1H); $^{13}$C NMR (75.5 MHz, CD$_3$OD) δ 157.9, 146.4, 144.3, 126.8, 123.9, 69.2, 57.5, 40.1, 30.9, 30.6, 29.6, 22.7; mp 165–167° C.

EXAMPLE 7

2-[2-(4-Pyridyl)methanethioethyl]-1-methylpyrrolidine (Method B)

Into a 500 mL round-bottomed flask equipped with a magnetic stirring bar was placed (4-pyridyl)methanethiol from the previous synthesis (62 mmol) and THF (120 mL). The resulting solution was cooled to 0° C. in an ice bath. Sodium hydride (5.0 g of a 60% dispersion in mineral oil, 125 mmol) was added to the cold solution which resulted in vigorous gas evolution. After 15 minutes gas evolution had subsided and a yellow suspension had formed. 2-(2-Chloroethyl)-1-methylpyrrolidine hydrochloride (8.7 g, 47 mmol) in DMF (100 mL) was added via a cannula to the reaction mixture at 0° C. The flask and cannula were then rinsed with additional DMF (20 mL) to insure complete transfer. After stirring the mixture for 45 minutes at 0° C., tetrabutylammonium iodide (688 mg) was added. The ice bath was then removed and the reaction was allowed to warm to 25° C. After 6 hours at 25° C. the reaction was quenched by the addition of glacial acetic acid (8.0 mL, 140 mmol) and water (100 mL) and the mixture was concentrated in vacuo. To the resulting brown solution was added saturated aqueous sodium bicarbonate solution (100 mL) and ethyl acetate (300 mL) and the layers were separated. The aqueous phase was extracted with ethyl acetate (4×100 mL) and the combined organic extracts were washed with water (100 mL), brine (100 mL), and dried over sodium sulfate. The drying agent was removed by filtration and the filtrate was concentrated in vacuo to afford 15.87 g of a biphasic brown oil. The crude product was chromatographed on silica gel eluting with chloroform:methanol (gradient elution at 15:1, 10:1, 7:1, 5:1, and 3:1). Fractions from the column containing pure product were concentrated to afford a dark oil (2.02 g, 14%). The pure fractions could be further purified by Kügelrohr distillation (200° C., 0.5 Torr) to afford a clear liquid that was analytically pure. $^1$H NMR (300 MHz, CD$_3$OD) δ 8.60 (m, 2H), 7.43 (m, 2H), 3.77 (s, 2H), 3.01 (m, 1H), 2.54–2.32 (m, 2H), 2.26 (s, 3H), 2.16 (m, 2H), 2.02–1.85 (m, 2H), 1.72 (m, 2H), 1.51–1.27 (m, 2H); $^{13}$C NMR (75.5 MHz, CD$_3$OD) δ 151.3, 150.1, 125.8, 66.7, 57.9, 40.6, 35.8, 34.1, 31.3, 29.5, 22.5; LRMS (EI) m/e 236 (C$_{13}$H$_{20}$N$_2$S, M$^+$).

EXAMPLE 8

2-[2-(2-Pyridyl)methanethioethyl]-1-methylpyrrolidine (Method B)

Prepared by a procedure analogous to that described for 2-[2-(4-pyridyl)methanethioethyl]-1-methylpyrrolidine (see Example 7) but with the appropriate starting material to provide the 2-isomer. Yellow oil, (3.03 g, 75%). $^1$H NMR (300 MHz, CDCl$_3$) δ 8.53 (m, 1H), 7.65 (ddd, J=2, 8, 8 Hz, 1H), 7.37 (d, J=8 Hz, 1H), 7.16 (m, 1H), 3.85 (s, 2H), 3.03 (m, 1H), 2.62–2.39 (m, 2H), 2.27 (s, 3H), 2.16–2.03 (m, 2H), 1.97–1.81 (m, 2H), 1.79–1.58 (m, 2H), 1.57–1.33 (m, 2H) ; $^{13}$C NMR (75.5 MHz, CDCl$_3$) δ 158.8, 149.3, 136.7, 123.0, 121.9, 65.2, 57.2, 40.4, 38.4, 33.4, 30.3, 28.7, 21.8.

EXAMPLE 9

1-[2-(4-Pyridine)thiopropyl]-piperidine (Method A)

1-(2-chloropropyl)-piperidine hydrochloride (2.51 g, 12.66 mmol), 4-mercaptopyridine (1.55 g, 13.94 mmol), potassium carbonate (5.25 g, 38.0 mmol) and DMF (40 mL) were combined and stirred at room temperature for 24 hours, yielding 1.72 g (7.27 mmol, 57%) of the desired compound which was converted to.the hydrochloride salt. $^1$H NMR (300 MHz, CD$_3$OD) δ 7.90 (d, J=7 Hz, 2H), 7.21 (d, J=7 Hz, 2H), 3.46 (m, 2H), 3.19–3.28 (m, 4H), 2.89 (m, 2H), 2.20 (m, 2H), 1.74–1.88 (m, 6H); $^{13}$C NMR (75.5 MHz, CD$_3$OD) δ 166.3, 141.1, 124.3, 124.1, 56.9, 54.8, 29.3, 24.7, 24.3, 23.1; LRMS (EI) m/e 236 (M$^+$); mp 91–92° C.

EXAMPLE 10

1-[2-(4-Pyridyl)methanethioethyl]-piperidine (Method C)

Prepared according to the general procedure C (see Example 3) with 1-(2-chloroethyl)-piperidine hydrochloride (1.2 g, 6.5 mmol), 4-pyrididemethane thioacetate (1.1 g, 6.58 mmol), LiOH (1N, 6.60 mmol) and MeOH (50 mL), yielding 0.96 g (4.06 mmol, 62%) of the desired compound. $^1$H NMR (300 MHz, CDCl$_3$) δ 8.54 (d, J=7 Hz, 2H), 7.29 (d, J=7 Hz, 2H), 3.69 (s, 2H), 2.42–2.68 (m, 6H), 1.41–1.71 (m, 6H) ; LRMS (EI) m/e 236 (M$^+$).

EXAMPLE 11

1-[2-(4-Pyridyl)methanethiopropyl]-piperidine (Method C)

Prepared according to the general procedure C (see Example 3) with 1-(2-chloropropyl)-piperidine hydrochloride (1.5 g, 7.5 mmol), 4-pyrididemethane thioacetate (1.05 g, 6.33 mmol), LiOH (1N, 7.0 mmol) and MeOH (40 mL), yielding 0.61 g (2.44 mmol, 38.5%) of the desired compound. $^1$H NMR (300 MHz, CDCl$_3$) δ 8.54 (d, J=7 Hz, 2H), 7.25 (d, J=7 Hz, 2H), 3.66 (s, 2H), 2.30–2.45 (m, 8H), 1.41–1.76 (m, 8H); LRMS (EI) m/e 250 (M$^+$).

EXAMPLE 12

3-[Endo-(2-Pyridine)thio]-8-methyl-8-azabbicyclo [3.2.1]octane (Method B)

Mesylate derivative of tropinol (6.16 g, 28.1 mmol), 2-mercaptopyridine (3.2 g, 28.6 mmol), sodium hydride (1.7 g, 68.0 mmol) were combined, producing 2.75 g (11.76 mmol, 42%) of the desired compound which was converted to the hydrochloride salt. $^1$H NMR (300 MHz, CD$_3$OD) δ 8.45 (m, 1H), 7.66 (t, J=7 Hz, 1H), 7.27 (d, J=7 Hz, 1H), 7.13 (t, J=7 Hz, 1H), 4.3 (m, 1H), 3.96 (s, 2H), 2.83 (s, 3H), 2.05–2.38 (m, 8H); LRMS (EI) m/e 234 (M$^+$); mp 201–205° C.

EXAMPLE 13

3-[Endo-2-(2-Pyridine)thiomethyl]-8-methyl-8-azabbicyclo[3.2.1]octane (Method B)

Endo-3-thio-8-methyl-8-azabicyclo[3.2.1]octane (0.35 g, 2.2 mmol), 2-picolyl chloride hydrochloride (0.42 g, 2.6 mmol), sodium hydride (0.12 g, 5 mmol) were combined, producing 0.19 g (0.77 mmol, 35%) of the desired compound which was converted to the hydrochloride salt. $^1$H NMR (300 MHz, CD$_3$OD) δ 8.6 (m, 1H), 8.5 (m, 1H), 7.9 (m, 1H), 7.6 (m, 1H), 4.4 (m, 2H), 3.8 (m, 2H), 2.6 (s 3H), 1.8–2.2 (m, 8H); LRMS (EI) m/e 248 (M$^+$); mp 204–206° C.

EXAMPLE 14

Endo-exo-methyl-2-oxo-8-(Phenylmethyl)-8-azabicyclo[3.2.1]oct-3-ene-6-carboxylate To a flask containing N-benzyl-3-hydroxypyridinium bromide (50 g, 226 mmol), methylacrylate (203 mL, 2.26 mol) and triethylamine(63 mL, 452 mmol) were added 2 spatulas of hydroquinone. The yellow suspension was then stirred at 70° C. for 20 h. The reaction mixture was allowed to cool to 25° C. and the solids were removed by filtration. The filtrate was concentrated in vacuo and dried to afford a brown oil (60 g, 98%). $^1$H NMR (300 MHz, CDCl$_3$): δ 7.28 (m, 5H), 6.98 (q, J=5.1 Hz, 1H), 6.13 (t, J=10 Hz, 1H), 3.78 (m, 8H), 2.43 (m, 3H).

EXAMPLE 15

Endo- and exo-methyl 2-oxo-8-(tertbutyloxycarbonyl)-8-azabicyclo[3.2.1]octane-6-carboxylate A parr bottle was charged with endo-, exo-methyl 2-oxo-8-(phenylmethyl)-8-azabicyclo[3.2.1]oct-3-ene-6-carboxylate (27.1 g, 100 mmol), 10% Pd—C (2 g), BOC anhydride (32.7 g, 150 mmol) and methanol (180 mL). The mixture was hydrogenated under $H_2$ (g) at 30 psi for 5 h after which time the reaction was complete as indicated by t.l.c.

The reaction mixture was filtered through celite and concentrated in vacuo to afford ca. 30 g of an orange oil. This was dissolved in small volume of toluene and purifed by chromatography on silica gel using EtOAc:hexane (6:1 to 1:1) as eluant to afford the endo isomer (7.43 g) as a yellow liquid, and then the exo isomer (9.81 g) as colorless solid. Some mixed fractions were also isolated (6.54 g); total yield: 84%. $^1H$ NMR (300 MHz, $CDCl_3$): δ endo: 4.59 (m, 1H), 4.34 (m, 1H), 3.78 (s, 3H), 3.37 (m, 1H), 2.41 (m, 5H), 1.83 (m, 1H), 1.45 (s, 10H); exo : 4.56 (m, 2H), 3.74 (s, 3H), 2.96 (dd, J=5.4 Hz, 1H), 2.36 (m, 4H), 1.92 (m, 2H), 1.44 (s, 10H).

EXAMPLE 16

Endo-methyl 2-oxo-8-(Tertbutyloxycarbonyl)-8-azabicyclo[3.2.1]octane-6-carboxylate, Tosylhydrazone Derivative To a solution of endo-methyl 2-oxo-8-(tertbutyloxycarbonyl)-8-azabicyclo[3.2.1]octane-6-carboxylate (4.51 g, 15.9 mmol) in acetic acid (80 mL) was added p-toluenesulfonhydrazide (5.93 g, 31.8 mmol) and the yellow solution was stirred at 25° C. for 18 h. Water (80 mL) was added and the solution was stirred at 25° C. for 30 min. to afford a colorless precipitate. The solid was isolated by filtration, diluted with methanol-toluene, concentrated and dried in vacuo to afford the tosylhydrazone of the endo ester as a colorless solid (6.00 g, 83%). $^1H$ NMR (300 MHz, $CDCl_3$): δ 7.84 (m, 2H), 7.25 (m, 6H), 4.52 (m, 2H), 3.75 (s, 3H), 3.24 (m, 1H), 2.30 (m, 11H), 1.31 (s, 9H).

EXAMPLE 17

Endo-methyl 8-(Tertbutyloxycarbonyl)-8-azabicyclo[3.2.1]octane-6-carboxylate To a solution of the endo tosylhydrazone derivative (3 g, 6.6 mmol) in methanol (60 mL) was added a solution of zinc chloride (630 mg, 4.63 mmol) and sodium cyanoborohydride (584 mg, 9.3 mmol) in methanol (30 mL) The reaction mixture was heated under reflux for 3 h and then concentrated in vacuo. Ethyl acetate and water were added, the reaction mixture was acidified to pH 1 with HCl (1M) then basified to pH 9 with solid potassium carbonate. The combined organic extracts were washed with a saturated solution of sodium potassium tartrate, then brine, dried over magnesium sulfate, filtered and concentrated to afford a yellow oil (1.8 g). The crude material was purified by chromatography on silica gel using EtOAc:hexane (6:1) as eluant to afford the endo ester as a colorless oil (1.00 g, 57%) which solidified after 18 h. $^1H$ NMR (300 MHz, $CD_3OD$): δ 4.28 (m, 1H), 4.17 (m, 1H), 3.71 (s, 3H), 3.27 (m, 1H), 2.20 (m, 2H), 1.64 (m, 6H), 1.47 (s, 9H); $^{13}C$ NMR (75.5 MHz, $CD_3OD$): δ 173.7, 154.7, 81.0, 57.5–56.7(rot), 55.5–54.6(rot), 47.3–46.8(rot), 31.8–31.1(rot), 30.8–30.1(rot), 28.6, 28.4–27.8(rot), 17.5. Anal. Calcd. for $C_{14}H_{23}O_4N$: C, 62.43; H, 8.61; N, 5.20%. Found: C, 62.35, H, 8.57, N, 5.25%. LRMS 269 ($M^+$).

EXAMPLE 18

Endo-6-(Hydroxymethylene)-8-(tertbutyloxycarbonyl)-8-azabicyclo[3.2.1]octane A suspension of lithium aluminum hydride (4.53 g, 120 mmol) in dry THF (80 mL) was stirred for 10 min at 25° C. then cooled to 0° C. Endo-methyl 8-(tertbutyloxycarbonyl)-8-azabicyclo[3.2.1]octane-6-carboxylate (6.41 g, 23.8 mmol) was added and the solution was allowed to warm to ambient temperature then stirred at 25° C. for 24 h. The reaction was quenched by adding water (4.5 mL), then 15% aq. NaOH (4.5 mL), then water (9 mL). The resulting precipitate was removed by filtration and the fitrate concentrated in vacuo to afford an oil (6.1 g). This material was purified by chromatography on silica gel using EtOAc:hexane (4:1 to 1:1) as eluant to afford the endo alkanol as a colorless oil (5.16 g, 90%) which solidified after 18 h. $^1H$ NMR (300 MHz, $CD_3OD$): δ 4.15 (m, 1H), 4.04 (m, 1H), 3.70 (m, 2H), 2.45 (m, 1H), 2.17 (m, 1H), 1.73 (m, 3H), 1.46 (s, 9H), 1.42 (m, 4H); $^{13}C$ NMR (75.5 MHz, $CD_3OD$): δ 155.0, 80.6, 62.1, 56.9–56.0(rot), 55.3–54.3(rot), 45.3–44.9 (rot), 31.7–30.9(rot), 29.0, 26.7, 26.1, 18.2; Anal. Calcd. for $C_{13}H_{23}O_3N$: C, 64.70; H, 9.61; N, 5.80%. Found: C, 64.60, H, 9.55, N, 5.83%. LRMS 241 ($M^+$).

EXAMPLE 19

Endo-6-(Toluenesufonyloxymethylene)-8-(tertbutyloxycarbonyl)-8-azabicyclo[3.2.1]octane In a flask containing endo-6-(hydroxymethylene)-8-(tertbutyloxycarbonyl)-8-azabicyclo[3.2.1]octane (4 g, 16.6 mmol) in methylene chloride (400 mL) was added triethylamine (3.7 mL, 26.5 mmol), toluenesulfonyl chloride (5.04 g, 26.5mmol) and N, N-dimethylaminopyridine (500 mg).

The solution was stirred at 25° C. for 22 h before the reaction mixture was concentrated and water (100 mL) was added. The solution was extracted with ethyl acetate (3×150 mL), the organic phase washed with water (50 mL), then brine (50 mL), dried over magnesium sulfate, filtered and concentrated in vacuo. The crude product was chromatographed on silica gel with EtOAc:hexane (6:1 to 3:1) as eluant to afford the endo toluenesulfonyl ester as a colorless solid (5.89 g, 89%). $^1H$ NMR (300 MHz, $CD_3OD$): δ 7.81 (d, J=8 Hz, 2H), 7.46 (d, J=8 Hz, 2H), 4.14 (m, 3H), 3.95 (bs, 1H), 2.52 (bs, 1H), 2.45 (s, 3H), 2.10 (m, 1H), 1.50 (m, 7H), 1.47 (s, 9H); $^{13}C$ NMR (75.5 MHz, $CD_3OD$): δ 154.8, 146.7, 134.2, 131.2, 129.1, 80.9, 70.7, 56.6–55.7(rot), 55.2–54.3 (rot), 41.7–41.2(rot), 31.1–30.4(rot), 28.7, 26.5–25.8(rot), 21.6, 17.8; Anal. Calcd. for $C_{20}H_{29}O_5NS$: C, 60.74; H, 7.39; N, 3.54%. Found: C, 60.67, H, 7.37, N, 3.59%.

EXAMPLE 20

Endo-6-(2-Pyridinethiomethylene)-8-(tertbutyloxycarbonyl)-8-azabicyclo[3.2.1]octane 2-Mercaptopyridine (551 mg, 4.95 mmol) was added to a slurry of NaH (198 mg of a 60% dispersion in oil, 4.95 mmol) in dry THF (10 mL) under Ar (g). The suspension was stirred at 25° C. for 10 min. before the endo-6-(toluenesufonyloxymethylene)-8-(tertbutyloxycarbonyl)-8-azabicyclo[3.2.1]octane (1 g, 2.5 mmol) in DMF (6 mL) was added. The resulting clear, yellow solution was stirred at 70° C. for 18 h. The reaction was allowed to cool to 25° C. and water (10 mL) was added. The solution was extracted with ethyl acetate (3×20 mL), the combined organic phase was washed with water (3×10 mL), brine (2×10 mL), dried over magnesium sulfate, filtered and concentrated in vacuo to afford a yellow oil (1.1 g). The crude product was chromatographed on silica gel with EtOAc:hexane (8:1) as eluant to afford the BOC-protected endo 2-thiopyridine as a colorless oil (740 mg, 88%). $^1$H NMR (300 MHz, CDCl$_3$): δ 8.42 (m, 1H), 7.47 (m, 1H), 7.16 (m, 1H), 6.98 (m, 1H), 4.11 (m, 2H), 3.47 (m, 1H), 3.24 (dd, J=8.4, 1H), 1.72 (m, 6H), 1.46 (m, 11H); $^{13}$C NMR (75.5 MHz, CD$_3$OD): δ 159.7, 154.5, 149.9, 137.3, 123.0, 120.4, 80.3, 57.3–56.3 (rot), 55.1–54.2(rot), 41.7–41.2(rot), 34.1–33.5(rot), 31.0–30.3(rot), 30.2, 26.2–25.6(rot), 17.7.

EXAMPLE 21

Endo-6-(2-Pyridinethiomethylene)-8-H-8-azabicyclo [3.2.1]octane Hydrochloride

The BOC-protected endo-2-thiopyridine (710 mg, 2.12 mmol) was dissolved in methylene chloride (15 mL) and HCl in dioxane (9.6 mL, 38 mmol) was added. The solution was stirred at 25° C. for 40 min and then concentrated in vacuo to afford a yellow foam (440 mg). This material was purified by chromatography on silica gel with CHCl$_3$:MeOH (10:1 to2:1) as eluant to afford a yellow sticky solid (635 mg). $^1$H NMR (300 MHz, CD$_3$OD): δ 8.56 (m, 1H), 8.07 (m, 1H), 7.76 (m, 1H), 7.48 (m, 1H), 4.05 (m, 1H), 3.95 (bs, 1H), 3.60 (m, 2H), 2.87 (m, 2H), 2.47 (m, 2H), 1.99 (m, 4H), 1.75 (m, 3H); $^{13}$C NMR (75.5 Mhz, CD$_3$OD): δ 158.3, 146.9, 143.1, 125.8, 122.9, 58.5, 56.8, 40.0, 32.2, 30.7, 29.3, 24.7, 16.8; LRMS 234 (M$^+$).

EXAMPLE 22

Exo-methyl 2-oxo-8-(Tertbutyloxycarbonyl)-8-azabicyclo[3.2.1]octane-6-carboxylate Tosylhydrazone Derivative Prepared according to the procedure described for the endo isomer (see Example 16) with the appropriate exo isomer starting material. Crude yield 19.43 g, 94%, carried on to the next step without further purification.

EXAMPLE 23

Exo-methyl 8-(Tertbutyloxycarbonyl)-8-azabicyclo [3.2.1]octane-6-carboxylate

Prepared according to the procedure described for the endo isomer (see Example 17) using the appropriate exo isomer starting material. Yield: 5.14 g, 45% over two steps from the ketone. $^1$H NMR (mixture of rotamers) (300 MHz, CDCl$_3$) δ 4.50–4.19 (m, 2H), 3.69 (s, 3H), 2.84 (dd, J=5, 9 Hz, 1H), 2.51–2.27. (m, 1H), 1.90–1.39 (m, with embedded s at 1.46, 16H); LRMS (EI) m/e 269 (C$_{14}$H$_{23}$NO$_4$, M$^+$).

EXAMPLE 24

Exo-6-(Hydroxymethylene)-8-(tertbutyloxycarbonyl)-8-azabicyclo[3.2.1]octane

Prepared according to the procedure described for the endo isomer (see Example 18) using the appropriate exo isomer starting material. Colorless solid, yield: 2.79 g, 100%. $^1$H NMR (mixture of rotamers) (300 MHz, CDCl$_3$) δ 4.26 (m, 0.5H), 4.16 (m, 0.5H), 4.06 (br s, 0.5H), 3.98 (br s, 0.5H), 3.52–3.34 (m, 2H), 2.28–2.14 (m, 1H), 1.95 (m, 0.25H), 1.86–1.37 (m with embedded s at 1.47, 17H); $^{13}$C NMR (mixture of rotamers) (75.5 MHz, CDCl$_3$) δ 154.2, 154.0, 79.3, 79.1, 65.7, 65.3, 56.6, 55.7, 54.5, 53.6, 53.4, 50.4, 44.2, 43.5, 31.4, 31.0, 30.6, 30.4, 29.8, 28.4, 17.1, 17.0; LRMS (EI) m/e 241 (C$_{13}$H$_{23}$NO$_3$, M$^+$).

EXAMPLE 25

Exo-6-(Toluenesufonyloxymethylene)-8-(tertbutyloxycarbonyl)-8-azabicyclo[3.2.1]octane Prepared according to the procedure described for the endo isomer (see Example 19) using the appropriate exo isomer starting material. Yield: 4.0 g, 90%. $^1$H NMR (mixture of rotamers) (300 MHz, CDCl$_3$) δ 7.79 (d, J=8 Hz, 2H), 7.35 (d, J=8 Hz, 2H), 4.19 (m, 0.5H), 4.08 (m, 0.5H), 3.94–3.66 (m, 3H), 2.47–2.32 (m with embedded br s at 2.45, 4H), 1.87–1.52 (m, 5H), 1.49–1.32 (m, 12H).

EXAMPLE 26

Exo-6-(2-Pyridinethiomethylene)-8-(tertbutyloxycarbonyl)-8-azabicyclo[3.2.1]octane Prepared according to the procedure described for the endo isomer (see Example 20) using the appropriate exo isomer starting material. Yield: 751 mg, 86%. $^1$H NMR (mixture of rotamers) (300 MHz, CDCl$_3$) δ 8.41 (m, 1H), 7.47 (m, 1H), 7.16 (m, 1H), 6.98 (m, 1H), 4.31 (m, 0.5H), 4.17 (m, 0.5H), 4.08 (br s, 0.5H), 4.02 (m, 0.5H), 3.23–3.06 (m, 2H), 2.41–2.30 (m, 1H), 2.02–1.35 (m with embedded s at1.48 & 1.45, 17H).

EXAMPLE 27

Exo-6-(2-Pyridinethiomethylene)-8-H-8-azabicyclo [3.2.1]octane Hydrochloride

Prepared according to the procedure described for the endo isomer (see Example 21) using the appropriate exo isomer starting material. Yield: 528 mg, 78%. $^1$H NMR (300 MHz CD$_3$OD) δ 8.65 (d, J=6 Hz, 1H), 8.39 (app t, J=7 Hz, 1H), 8.08 (d, J=8 Hz, 1H), 7.74 (app t, J=7 Hz, 1H), 4.11 (br d, J=6 Hz, 1H), 4.01 (br s, 1H), 3.68–3.49 (m, 2H), 2.75–2.63 (br s, 1H), 2.37 (m, 1H), 2.08–1.62 (m, 7H); $^{13}$C NMR (75.5 MHz, CD$_3$OD) δ 157.6, 146.6, 144.1, 127.0, 124.0, 61.3, 58.0, 40.4, 37.3, 34.6, 29.4, 28.9, 16.5; LRMS (EI) m/e 234 (C$_{13}$H$_{18}$N$_2$S, free base M$^+$).

EXAMPLE 28

Endo-6-[(4-Pyridyl)methanethiomethylene]-8-(tertbutyloxycarbonyl)-8-azabicyclo[3.2.1]octane (Method B)

Prepared following the general procedure B (see Example 7) using endo-6-(toluenesufonyloxymethylene)-8-(tertbutyloxycarbonyl)-8-azabicyclo[3.2.1]octane and (4-pyridyl)methanethiol to provide the product as a pale yellow oil (687mg, 80%). $^1$H NMR (300 MHz, CD$_3$OD) δ 8.46 (d, J=6.0, 2H), 7.44 (d, J=5.8, 2H), 4.12 (m, 1H), 3.93 (m, 1H), 3.80 (s, 2H), 2.61 (m, 2H), 2.41 (m, 1H), 2.25 (m, 1H), 1.69 (m, 3H), 1.54 (m, 2H), 1.45 (s, 9H), 1.33 (m, 2H).

EXAMPLE 29

Endo-6-[(4-Pyridyl)methanethiomethylene]-8-H-8-azabicyclo[3.2.1]octane Hydrochloride Prepared by a procedure analogous to that described previously (see preparation of endo-6-(2- pyridinethiomethylene)-8-H-8-azabicyclo[3.2.1]octane hydrochloride; see Example 21) with endo-6-[(4-pyridyl)methanethiomethylene]-8-(tertbutyloxycarbonyl)-8-azabicyclo[3.2.1]octane as the starting material. The product dihydrochloride salt was isolated as a yellow solid (540 mg). Mp: >205° C.; $^1$H NMR (300 MHz, CD$_3$OD) δ 8.87 (d, J=6.5 Hz, 2H), 8.13 (d, J=6.5 Hz, 2H), 4.13 (s, 2H), 4.01 (m, 1H), 3.85 (m, 1H), 2.80 (m, 2H), 2.67 (m, 1H), 2.41 (m, 1H), 1.9 (m, 3H), 1.67 (m, 4H).

EXAMPLE 30

Exo-6-[(4-Pyridyl)methanethiomethylene]-8-(tertbutyloxycarbonyl)-8-azabicyclo[3.2.1]octane Prepared by a procedure analogous to that described (see Example 7) for the preparation of the endo-6-[(4-pyridyl)methanethiomethylene]-8-(tertbutyloxycarbonyl)-8-azabicyclo[3.2.1]octane with the exo analog and (4-pyridyl)methanethiol providing the desired product as a clear oil (500 mg, 53%). $^1$H NMR (300 MHz, CD$_3$OD): δ 8.46 (m, 2H), 7.43 (m, 2H), 4.14 (m, 1H), 3.96 (m, 1H), 3.77 (s, 2H), 2.38 (m, 2H), 2.18 (m, 1H), 1.91 (m, 1H), 1.59 (m, 7H), 1.44 (d, 9H).

EXAMPLE 31

Exo-6-[(4-Pyridyl)methanethiomethylene]-8-H-8-azabicyclo[3.2.1]octane Hydrochloride Prepared by a procedure analogous to that described previously (see Example 21) preparation of endo-6-(2-pyridinethiomethylene)-8-H-8-azabicyclo[3.2.1]octane hydrochloride) with exo-6-[(4-pyridyl)methanethiomethylene]-8-(tertbutyloxycarbonyl)-8-azabicyclo[3.2.1]octane as the starting material. The product dihydrochloride salt was isolated as a yellow solid (700 mg). Mp 140° C.; $^1$H NMR (300 MHz, CD$_3$OD): δ$_H$ 8.82 (d, J=6.5 Hz, 2H), 8.16 (d, J=6.5 Hz, 2H), 4.12 (s, 1H), 4.02 (m, 1H), 3.65 (m, 1H), 2.70 (m, 2H), 2.52 (m, 1H), 2.27 (dd, J=13, 8, 1H), 1.79 (m, 7H).

EXAMPLE 32

Synthesis of Invention Compounds XXVII
Synthetic Scheme X
Method E:

Into a three neck flask fitted with a condenser, an addition funnel, a thermometer and flushed with argon was placed the hydroxypyridine derivative of general Formula XXVI (1.5 eq), the alcohol derivative of general Formula III (1.0 eq) triphenylphosphine (1 eq) and dry tetrahydrofuran (1.2 mL/mmol). The mixture was cooled to 0° C. and diethyl azodicarboxylate (DEAD) (1.0 eq) was added dropwise. The reaction was allowed to warm to room temperature and stirred overnight. After hydrolysis the mixture was extracted three times with EtOAc (2 mL/mmole).

The organic layers were combined, washed with water and extracted with HCl (1.0 N. 3×50 mL). The aqueous layers were combined, basified to pH=11 with sodium hydroxide (5 N) and extracted with EtOAc (3×50 mL). The organic layers were combined, washed with NaOH (1N, 50 mL), brine (50 mL), dried (MgSO$_4$) and concentrated under vacuum (15 mm Hg) to give an oil. The crude material was purified via chromatography on silica using a gradient of chloroform and methanol as eluant. The pure compound of general Formula XXVII was converted to the HCl salt.

EXAMPLE 33

2-[2-(2-Pyridine)thioethyl]-1-methylpyrrolidine
(Method E)

2-(2-chloroethyl)-1-methylpyrrolidine (3.17 g, 24.54 mmol), 2-hydroxypyridine (5.0 g, 45.0 mmol), triphenylphosphine (6.44 g, 24.54 mmol), diethyl azodicarboxylate (3.86 mL, 24.54 mmol) and tetrahydrofuran (40 mL) were combined, producing 2.0 g (9.69 mmol, 40%) of the desired compound which was converted to the hydrochloride salt. $^1$H NMR (300 MHz, CD$_3$OD) δ 7.98 (d, J=7 Hz, 1H), 7.54 (t, J=7 Hz, 1H), 6.81 (t, J=7 Hz, 1H), 6.67 (d, J=7 Hz, 1H), 4.26 (m, 2H), 3.4 (m, 2H), 3.05 (m, 1H), 2.78 (s, 3H), 2.28 (m, 2H), 1.7–2.01 (m, 5H); LRMS (EI) m/e 207 (M$^+$).

EXAMPLE 34

2-[2-(4-Pyridine)thioethyl]-1-methylpyrrolidine
(Method E)

2-(2-chloroethyl)-1-methylpyrrolidine (3.17 g, 24.54 mmol), 4-hydroxypyridine (3.5 g, 36.8 mmol), triphenylphosphine (6.44 g, 24.54 mmol), diethyl azodicarboxylate (3.86 mL, 24.54 mmol) and tetrahydrofuran (40 mL) were combined, producing 0.29 g (1.40 mmol, 6%) of the desired compound which was converted to the hydrochloride salt. $^1$H NMR (300 MHz, CD$_3$OD) δ 8.70 (d, J=7 Hz, 2H), 7.61 (d, J=7 Hz, 2H), 4.56 (m, 2H), 3.73 (m, 1H), 3.60 (m, 1H), 3.21 (m, 1H), 2.99 (s, 3H), 2.61 (m, 1H), 2.45 (m, 1H), 2.09–2.26 (m, 3H), 1.93 (m, 1H); $^{13}$C (75.5 MHz, CD$_3$OD) δ 172.9, 144.4, 114.7, 69.1, 68.1, 57.5, 40.1, 31.0, 30.7, 22.7; LRMS (EI) m/e 207 (M$^+$); mp 173–174° C.

EXAMPLE 35

Radioligand Binding $^3$H-Nicotine binding to rat cerebral membranes can be performed according to modifications of the method of Flyn and Mash (*J. Neurochem.* 47:1948 (1986)). For example, $^3$H-Nicotine (80 ci/mmol; New England Nuclear Corporation, Boston, Mass.) can be used as the ligand for nicotinic acetylcholine receptor binding assays.

An exemplary binding assay can be performed as follows. Decapitate Male Sprague-Dawley rats (250–400 gm) and remove the brains and dissect the cerebral cortex on ice. Synaptic membranes can be prepared by homogenizing the cortical tissue in 20 volumes of ice-cold modified Tris buffer (50 mM Tris pH 7.4, 120 mM NaCl, 5 mM KCl, 2 mM EDTA, 1 mM PMSF) with a polytron (20 sec at setting 5–6) followed by centrifugation (15 min at 25,000×g) at 4° C. Rehomogenize the resultant pellet and centrifuge twice. Resuspend the final pellet in ice-cold assay buffer (50 mM Tris pH 7.4, 120 mM NaCl, 5 mM KCl, 2 mM CaCl$_2$, 1 mM MgCl$_2$) at a concentration of membrane equivalent to 1 gm wet weight cortex per 10 ml buffer. After protein determination dilute the final membrane preparation with buffer to 3 mg protein/ml. This membrane preparation can be used in either the fresh state or frozen (−70° C.) then thawed.

The binding assay can be performed manually using 96-well plates, or using a Biomek automated work station (Beckman Instrument Co.). Dilute $^3$H-Nicotine in assay buffer to give a final concentration of 1.9 nM. Program the Biomek automated work station to automatically transfer 750 μl of assay buffer with $^3$H-nicotine, 230 μl of membrane preparation and 20 μl of solution containing the compound of interest in assay buffer, DMSO, ethanol:DMSO (1:1) or appropriate vehicle to the 96-well plate. Add Atropine to the incubation buffer at a final concentration of 3 μM to block binding to muscarinic acetylcholine receptor sites. Maintain the plates on ice for 60 min and separate the tissue-bound radioactivity from the free by rapid filtration in a Brandel Harvester onto GF/C filters presoaked in 0.5% polyethyleneimine for at least 2 hr. Wash the filters with 4×2 ml of ice-cold assay buffer and transfer the filters to vials to which 4 ml of scintillation cocktail has been added. Measure the radioactivity in a LS-6500 Beckman Liquid Scintillation Counter in an auto-dpm mode. Data can be analyzed by log-logit transformation or non-linear regression analysis (e.g., employing GraphPad Prism, available from GraphPad Software, San Diego, Calif.) to give $IC_{50}$ values. Non-specific binding can be defined by 10 $\mu$M cytisine.

EXAMPLE 36

Neurotransmitter Release

Measurement of $^3$H-dopamine ($^3$H-DA) release from rat striatal slices can be performed according to the method of Sacaan et al., (*J. Pharmacol. Comp. Ther* 224:224–230 (1995)). For example, the striata or olfactory tubercles can be dissected from male Sprague-Dawley rats (250–300 g) quickly on a cold glass surface. Chop the tissue to a thickness of 300 $\mu$m with a McIlwain tissue chopper. After chopping again at right angles disperse the tissue and incubate for 10 min. at 37° C. in oxygenated Kreb's buffer. $^3$H-Dopamine (40 Ci/mmol, NEN-Dupont, Boston, Mass.) can be added (50 nM) and the tissue incubated for 30 min. in Kreb's buffer containing 10 $\mu$M pargyline and 0.5 mM ascorbic acid. Transfer aliquots of the minced tissue to chambers of a Brandel Superfusion system and support the tissue on Whatman GF/B filter discs. Superfuse the tissue with buffer at a constant flow rate of 0.3 ml/min by means of a Brandel peristaltic pump. Collect the perfusate in plastic scintillation vials in 3-min fractions, and estimate the radio-activity by scintillation spectrophotometry. Discard the superfusate for the first 120 min. Collect two baseline fractions then switch the superfusion buffer to fresh buffer with or without compound of interest. At the end of the experiment remove the filter and the tissue and estimate the radiolabeled neurotransmitter content after extraction into scintillation fluid. The fractional efflux of radiolabeled neurotransmitter is estimated as the amount of radioactivity in the perfusate fraction relative to the total amount in the tissue.

EXAMPLE 37

Functional Assays for Modulators of Acetylcholine Receptors

Functional assays for acetylcholine receptors are described in U.S. Pat. No. 5,369,028, issued Nov. 29, 1994 (also published as WO91/15602), as well as published PCT Application Nos. WO94/20617 (see especially Example 4.3a) and WO96/41876 (see especially Example 6E, the disclosures of which are hereby incorporated by reference herein. The results of functional assays as per the above-referenced publications with several invention compounds are summarized in Table I.

TABLE I

| Formula Z | Calcium flux (a2b4) $EC_{50}$ (mM) |
|---|---|
| Nicotine | 2.5 |
| A = N | 13 |
| B = C | |

TABLE I-continued

| Formula Z | Calcium flux (a2b4) $EC_{50}$ (mM) |
|---|---|
| $R_2, R_3, R_4, R_5$ = H<br>D = absent<br>E = —S—<br>G = —CH$_2$CH$_2$—<br>J = N-methyl-2-pyrrolidine<br>A = C<br>B = N | 4 |
| $R_1, R_2, R_4, R_5$ = H<br>D = absent<br>E = —S—<br>G = —CH$_2$CH$_2$—<br>J = N-methyl-2-pyrrolidine<br>A = N<br>B = C | 31 |
| $R_2, R_3, R_4, R_5$ = H<br>D = —CH$_2$—<br>E = —S—<br>G = —CH$_2$CH$_2$—<br>J = N-methyl-2-pyrrolidine<br>A = C<br>B = N | 8 |
| $R_1, R_2, R_4, R_5$ = H<br>D = —CH$_2$—<br>E = —S—<br>G = —CH$_2$CH$_2$—<br>J = N-methyl-2-pyrrolidine<br>A = N<br>B = C | 6 |
| $R_2, R_3, R_4, R_5$ = H<br>D = absent<br>E = —S—<br>G = absent<br>J = 3-exo-8-methyl-8-azabicyclo[3.2.1]octane<br>A = N<br>B = C | 6 |
| $R_2, R_3, R_4, R_5$ = H<br>D = —CH$_2$—<br>E = —S—<br>G = absent<br>J = 3-exo-8-methyl-8-azabicyclo[3.2.1]octane<br>A = N<br>B = C | 31 |
| $R_2, R_3, R_4, R_5$ = H<br>D = absent<br>E = —S—<br>G = —CH$_2$—<br>J = 6-endo-8-azabicyclo[3.2.1]octane<br>A = N<br>B = C | 1 |
| $R_2, R_3, R_4, R_5$ = H<br>D = absent<br>E = —S—<br>G = —CH$_2$—<br>J = 6-exo-8-azabicyclo[3.2.1]octane<br>A = C<br>B = N | 5.2 |
| $R_2, R_3, R_4, R_5$ = H<br>D = —CH$_2$—<br>E = —S—<br>G = —CH$_2$—<br>J = 6-endo-8-azabicyclo[3.2.1]octane<br>A = C<br>B = N | 0.9 |
| $R_2, R_3, R_4, R_5$ = H<br>D = —CH$_2$—<br>E = —S—<br>G = —CH$_2$—<br>J = 6-exo-8-azabicyclo[3.2.1]octane<br>A = N<br>B = C | 8 |
| $R_2, R_3, R_4, R_5$ = H<br>D = absent<br>E = —O— | |

TABLE I-continued

| Formula Z | Calcium flux (a2b4) EC$_{50}$ (mM) |
|---|---|
| G = —CH$_2$CH$_2$—<br>J = N-methyl-2-pyrrolidine<br>A = C<br>B = N<br>R$_1$, R$_2$, R$_4$, R$_5$ = H<br>D = absent<br>E = —O— | 31 |
| G = —CH$_2$CH$_2$—<br>J = N-methyl-2-pyrrolidine<br>A = N<br>B = C<br>R$_2$, R$_3$, R$_4$, R$_5$ = H<br>D = absent<br>E = —S— | 10 |
| G = —CH$_2$CH$_2$—<br>J = N-methyl-(R)-2-pyrrolidine<br>A = N<br>B = C<br>R$_2$, R$_3$, R$_4$, R$_5$ = H<br>D = absent<br>E = —S—<br>G = —CH$_2$CH$_2$—<br>J = N-methyl-(S)-2-pyrrolidine | 12 |

It can readily be seen from inspection of the data in the Table that a wide variety of compounds which fall within the scope of the present invention are effective modulators of calcium flux.

While the invention has been described in detail with reference to certain preferred embodiments thereof, it will be understood that modifications and variations are within the spirit and scope of that which is described and claimed.

That which is claimed is:

1. A compound having the Formula Z, as follows:

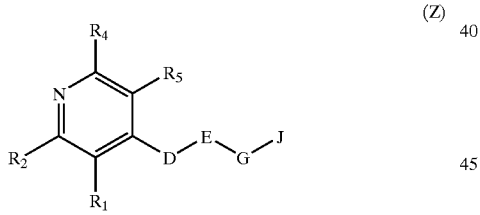

(Z)

or enantiomers, diastereomeric isomers or mixtures of any two or more thereof, or pharmaceutically acceptable salts thereof, wherein:
each of R$_1$, R$_2$, R$_4$ and R$_5$, are independently hydrogen, halogen, cyano, cyanomethyl, nitro, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, heterocyclic, substituted heterocyclic, trifluoromethyl, pentafluoroethyl, —O—C(O)—R$_A$, —O—C(O)—N(R$_A$)$_2$, —SR$_A$, —NHC(O)R$_A$ or —NHSO$_2$R$_A$, wherein R$_A$ is H, lower alkyl, substituted lower alkyl, aryl or substituted aryl, or —NR$_B$R$_B$, wherein each R$_B$ is independently hydrogen or lower alkyl, wherein said substituted alkyl, substituted cycloalkyl, substituted alkenyl, substituted alkynyl, substituted aryl, substituted alkylaryl, substituted arylalkyl, and substituted heterocyclic are each optionally substituted with one or more substituents, each substituent independently is hydroxy, C$_{1-4}$alkoxy, C$_{1-4}$mercapto, aryl, heterocyclic, halogen, trifluoromethyl, pentafluoroethyl, cyano, cyanomethyl, nitro, amino, carboxyl, carbamate, or sulfonamide;
D is optionally present; and when D is present, D is lower alkylene, substituted lower alkylene, cycloalkylene, substituted cycloalkylene, lower alkenylene, substituted lower alkenylene, or lower alkynylene;
E is —C(O)—, —C(O)—NR$_C$—, —C(O)—O—, —O—C(O)—NR$_C$—, —S—, —S(O)—, —S(O)—NR$_C$—, —S(O)$_2$—, —S(O)$_2$—NR$_C$—or —S(O)=NH—, wherein R$_C$ is hydrogen, lower alkyl or substituted lower alkyl; wherein when E is —O—C(O)—NR$_C$—, the oxygen is closest to the pyridine ring to which R$_1$, R$_2$, R$_4$, and R$_5$ are attached;
G is optionally present; and when G is present, G is lower alkylene, substituted lower alkylene, lower alkenylene, substituted lower alkenylene or lower alkynylene; with the proviso that when E is —S—, G is not present or is —CH$_2$—;
with the proviso that when E is S or S(O)$_2$, at least one of D or G is present;
J is a dialkylamino group having the structure J':

(J')

wherein:
R$^E$ and R$^F$ are independently hydrogen, lower alkyl, lower alkenyl, lower alkynyl, lower cycloalkyl or cycloalkyl, or
R$^E$ and R$^F$ combine to form a 3–7 membered ring, or J is a nitrogen-containing cyclic moiety having the structure J":

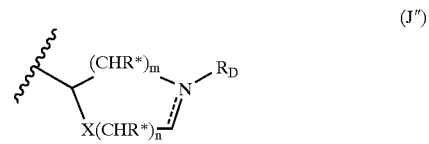

(J")

wherein R* is hydrogen, or one or both R* can cooperate with one another or with R$_D$ to form further ring(s), thereby forming polycyclic moieties containing fused rings having at least two atoms in common,
m is 0–2,
n is 0–3,
X is optionally present, and when present is —O—, —CH$_2$O—, —S—, —CH$_2$S—, —S(O)—, —CH$_2$S(O)—, —S(O)$_2$—, —CH$_2$S(O)$_2$— or —CH$_2$N—, and
R$_D$ is hydrogen, lower alkyl or lower cycloalkyl, or R$_D$ is absent when the nitrogen atom to which it is attached participates in the formation of a double bond.

2. A compound according to claim 1 wherein E is —S—, —S(O)—, —C(O)O— or —S(O)$_2$—.

3. A compound according to claim 1 wherein E is —S—.

4. A compound according to claim 1 wherein each of R$_1$, R$_2$, R$_4$ and R$_5$ are independently hydrogen, halogen, alkyl, or substituted alkyl.

5. A compound according to claim 1 wherein J is a pyrrolidino, a 1-methylpyrrolidino, a piperidino, a 1-methylpiperidino or an azabicyclic moiety.

6. A compound according to claim 5 wherein said azabicyclic moiety is an azabicycloalkane.

7. A compound according to claim 5 wherein said azabicyclic moiety is an azabicycloalkene.

8. A compound according to claim 1 wherein J is a pyrrolidino or 1-methylpyrrolidino moiety.

9. A compound according to claim 1 wherein J is a piperidino or 1-methylpiperidino moiety.

10. A compound according to claim 1 wherein J is pyrrolidino wherein the pyrrolidino ring nitrogen is optionally substituted by methyl.

11. A compound according to claim 1 wherein:
$R_1$, $R_2$, $R_4$ and $R_5$=H,
D=—CH$_2$—,
G=—CH$_2$—, and
J=6-endo-8-azabicyclo[3.2.1]octane.

12. A compound according to claim 1 wherein:
$R_1$, $R_2$, $R_4$ and $R_5$=H,
D=—CH$_2$—,
E=—S—,
G=—CH$_2$—, and
J=6-exo-8-azabicyclo[3.2.1]octane.

13. A compound consisting of 2-[2-(4-pyridine)thioethyl]-1-methyl pyrrolidine or 2-[2-(4-pyridine)methanethioethyl]-1-methyl pyrrolidine, or pharmaceutically acceptable salts thereof.

14. A pharmaceutical composition comprising a compound according to claim 1 and a pharmaceutically acceptable carrier therefor.

15. A method of modulating the activity of acetylcholine receptors, said method comprising:
contacting cell-associated receptors with a sufficient concentration of a compound according to formula Z to modulate the activity of said acetylcholine receptors, wherein formula Z is defined as follows:

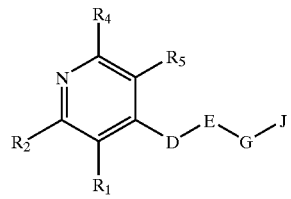

(Z)

or enantiomers, diastereomeric isomers or mixtures of any two or more thereof, or pharmaceutically acceptable salts thereof, wherein:
each of $R_1$, $R_2$, $R_4$, and $R_5$ are independently hydrogen, halogen, cyano, cyanomethyl, nitro, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, heterocyclic, substituted heterocyclic, trifluoromethyl, pentafluoroethyl, —O—C(O)—$R_A$, —O—C(O)—N($R_A$)$_2$, —S$R_A$, —NHC(O)$R_A$ or —NHSO$_2R_A$, wherein $R_A$ is hydrogen, lower alkyl, substituted lower alkyl, aryl or substituted aryl, or —N$R_BR_B$, wherein each $R_B$ is independently hydrogen or lower alkyl, wherein said substituted alkyl, substituted cycloalkyl, substituted alkenyl, substituted alkynyl, substituted aryl, substituted alkylaryl, substituted arylalkyl, and substituted heterocyclic are each optionally substituted with one or more substituents, each substituent independently is hydroxy, $C_{1-4}$alkoxy, $C_{1-4}$mercapto, aryl, heterocyclic, halogen, trifluoromethyl, pentafluoroethyl, cyano, cyanomethyl, nitro, amino, carboxyl, carbamate, or sulfonamide;

D is optionally, present; and when D is present, D is lower alkylene, substituted lower alkylene, cycloalkylene, substituted cycloalkylene, lower alkenylene, substituted lower alkenylene, or lower alkynylene;

E is —C(O)—, —C(O)—NR$_C$—, —C(O)—O—, —O—C(O)—NR$_C$—, —S—, —S(O)—, —S(O)—NR$_C$—, —S(O)$_2$—, —S(O)$_2$—NR$_C$— or —S(O)=NH—, wherein R$_C$ is hydrogen, lower alkyl or substituted lower alkyl; wherein when E is —O—C(O)—NR$_C$—, the oxygen is closest to the pyridine ring to which $R_1$, $R_2$, $R_4$, and $R_5$ are attached;

G is optionally present; and when G is present, G is lower alkylene, substituted lower alkylene, lower alkenylene, substituted lower alkenylene or lower alkynylene; with the proviso that when E is —S—, G is not present or is —CH$_2$—;

with the proviso that when E is S or S(O)$_2$, at least one of D or G is present;

J is a dialkylamino group having the structure J':

(J')

wherein:
R$^E$ and R$^F$ are independently hydrogen, lower alkyl, lower alkenyl, lower alkynyl, lower cycloalkyl or cycloalkyl, or
R$^E$ and R$^F$ combine to form a 3–7 membered ring, or
J is a nitrogen-containing cyclic moiety having the structure J"

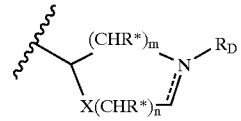

(J")

wherein R* is hydrogen, or one or both R* can cooperate with one another or with R$_D$ to form further ring(s), thereby forming polycyclic moieties containing fused rings having at least two atoms in common,
m is 0–2,
n is 0–3,
X is optionally present, and when present is —O—, —CH$_2$O—, —S—, —CH$_2$S—, —S(O)—, —CH$_2$S(O)—, —S(O)$_2$—, —CH$_2$S(O)$_2$— or —CH$_2$N—, and
R$_D$ is hydrogen, lower alkyl or lower cycloalkyl, or R$_D$ is absent when the nitrogen atom to which it is attached participates in the formation of a double bond.

16. Method for treating Parkinson's disease, said method comprising administering a therapeutically effective amount of a compound according to claim 1 to a patient suffering from Parkinson's disease.

17. Method for treating Alzheimer's disease, said method comprising administering a therapeutically effective amount of a compound according to claim 1 to a patient suffering from Alzheimer's disease.

18. Method for treating dementia, said method comprising administering a therapeutically effective amount of a compound according to claim 1 to a patient suffering from dementia.

19. Method for controlling pain, said method comprising administering a therapeutically effective amount of a compound according to claim 1 to a patient suffering from pain.

* * * * *